(12) United States Patent
Vahdat et al.

(10) Patent No.: US 9,927,444 B2
(45) Date of Patent: Mar. 27, 2018

(54) BONE MARROW-DERIVED HEMATOPOIETIC PROGENITOR CELLS AND ENDOTHELIAL PROGENITOR CELLS AS PROGNOSTIC INDICATORS FOR CANCER

(75) Inventors: Linda Vahdat, Wilton, CT (US); Shahin Rafii, Great Neck, NY (US); Rakhi Naik, Columbia, MD (US); Maureen Lane, Mt. Vernon, NY (US); Vivek Mittal, Greenlawn, NY (US)

(73) Assignee: Cornell University, Ithaca, NY (US)

( * ) Notice: Subject to any disclaimer, the term of this patent is extended or adjusted under 35 U.S.C. 154(b) by 538 days.

(21) Appl. No.: 14/001,249

(22) PCT Filed: Feb. 24, 2012

(86) PCT No.: PCT/US2012/026552
§ 371 (c)(1),
(2), (4) Date: Jan. 29, 2014

(87) PCT Pub. No.: WO2012/116295
PCT Pub. Date: Aug. 30, 2012

(65) Prior Publication Data
US 2014/0134190 A1    May 15, 2014

Related U.S. Application Data

(60) Provisional application No. 61/446,296, filed on Feb. 24, 2011, provisional application No. 61/525,285, filed on Aug. 19, 2011.

(51) Int. Cl.
| | |
|---|---|
| *A61K 38/00* | (2006.01) |
| *C12N 5/00* | (2006.01) |
| *G01N 33/68* | (2006.01) |
| *G01N 33/569* | (2006.01) |
| *G01N 33/574* | (2006.01) |
| *C07K 16/28* | (2006.01) |

(52) U.S. Cl.
CPC ..... *G01N 33/6893* (2013.01); *C07K 16/2863* (2013.01); *G01N 33/56966* (2013.01); *G01N 33/574* (2013.01); *G01N 2800/52* (2013.01); *G01N 2800/54* (2013.01)

(58) Field of Classification Search
None
See application file for complete search history.

(56) References Cited

U.S. PATENT DOCUMENTS

| 2004/0071687 A1 | 4/2004 | Rafii et al. |
| 2008/0003637 A1 | 1/2008 | Sugiyama et al. |
| 2008/0118432 A1 | 5/2008 | Bergstein et al. |
| 2010/0150932 A1* | 6/2010 | Lyden ............... C07K 16/2842 424/143.1 |
| 2011/0020221 A1 | 1/2011 | Berman et al. |
| 2011/0044997 A1* | 2/2011 | Rankin ................ A61K 35/28 424/158.1 |

FOREIGN PATENT DOCUMENTS

| WO | 03/006059 A1 | 1/2003 |
| WO | 2008/085951 A2 | 7/2008 |

OTHER PUBLICATIONS

Pescini et al ( Cerebrovascular Disease, 2009, V.27 , suppl.6, p. 54, Abstract 12.*
Ergun et al ( Stem Cells Rev. 2008, v.4 pp. 169-177).*
Jemal, A. et al., "Cancer Statistics, 2010" CA Cancer J Clin (2010) pp. 277-300, vol. 60.
Brewster, A.M. et al., "Residual risk of breast cancer recurrence 5 years after adjuvant therapy" J Natl Cancer Inst (2008) pp. 1179-1183, vol. 100.
Chiang, A.C. et al., "Molecular basis of metastasis" N Engl J Med (Dec. 2008) pp. 2814-2823, vol. 359.
Saphner, T. et al., "Annual hazard rates of recurrence for breast cancer after primary therapy" J Clin Oncol (Oct. 1996) pp. 2738-2746, vol. 14, No. 10.
Perou, C.M. et al., "Molecular portraits of human breast tumours" Nature (Aug. 2000) pp. 747-752, vol. 406.
Sorlie, T. et al., "Gene expression patterns of breast carcinomas distinguish tumor subclasses with clinical implications" Proc Natl Acad Sci USA (Sep. 2001) pp. 10869-10874, vol. 98, No. 19.
Sorlie, T. et al., "Repeated observation of breast tumor subtypes in independent gene expression data sets" Proc Natl Acad Sci USA (Jul. 2003) pp. 8418-8423, vol. 100, No. 14.
Cheang, M.G. et al., "Gene expression profiling of breast cancer" Annu Rev Pathol (2008) pp. 67-97, vol. 3.
Harris, L. et al., "American Society of Clinical Oncology 2007 update of recommendations for the use of tumor markers in breast cancer" J Clin Oncol (Nov. 2007) pp. 5287-5312, vol. 25.
Folkman, J., "Tumor angiogenesis: therapeutic implications" N Engl J Med (1971) pp. 1182-1186, vol. 285.
Carmeliet, P. et al., "Angiogenesis in cancer and other diseases" Nature (Sep. 2000) pp. 249-257, vol. 407.
Lyden, D. et al., "Impaired recruitment of bone marrow derived endothelial and a hematopoietic precursor cells blocks tumor angiogenesis and growth" Nature Medicine (Nov. 2001) pp. 1194-1201, vol. 7, No. 11.

(Continued)

*Primary Examiner* — Michail A Belyavskyi
(74) *Attorney, Agent, or Firm* — Scully Scott Murphy & Presser

(57) ABSTRACT

Methods of determining cancer progression or cancer relapse in a subject at risk for cancer progression or cancer relapse, the methods comprising: obtaining a sample from said subject; measuring the level of VEGFR1+ hematopoietic progenitor cells (HPCs) and/or VEGFR2+ endothelial progenitor cells (EPCs) in said sample; and taking additional samples and conducting additional measurements of HPCs and/or EPCs at one or more later time points. From the measurements, it can be determined whether there is a surge in the level of HPCs and/or EPCs in at least one later measurement, relative to an earlier measurement. A surge in the level of HPCs and/or EPCs indicates increased risk of progression or relapse of said subject's cancer.

9 Claims, 6 Drawing Sheets

(56) References Cited

OTHER PUBLICATIONS

Jain, S. et al., "Tetrathiomolybdate-associated copper depletion decreases circulating endothelial progenitor cells in women with breast cancer at high risk of relapse" Annals of Oncology (Jun. 2013) pp. 1491-1498, vol. 24, No. 6.
Fujita, K. et al., "Vascular endothelial growth factor receptor 1 expression in pelvic lymph nodes predicts the risk of cancer progression after radical prostatectomy" Cancer Sci (Jun. 2009) pp. 1047-1050, vol. 100.
Taylor, M. et al., "High levels of circulating VEGFR2+ Bone marrow-derived progenitor cells correlate with metastatic disease in patients with pediatric solid malignancies" Clin Cancer Res (Jul. 2009) pp. 4561-4571, vol. 15, No. 14.
Gao, D. et al., "The role of bone-marrow-derived cells in tumor growth, metastasis initiation and progression" Trends Mol Med (2009) pp. 333-343, vol. 15, No. 8.
Roodhart, J.M. et al., "Translating preclinical findings of (endothelial) progenitor cell mobilization into the clinic; from bedside to bench and back" Biochim Biophys Acta (2009) pp. 41-49, vol. 1796.
Dome, B. et al., "Identification and clinical significance of circulating endothelial progenitor cells in human non-small cell lung cancer" Cancer Res (Jul. 2006) pp. 7341-7347, vol. 66.
Furstenberger, G. et al., "Circulating endothelial cells and angiogenic serum factors during neoadjuvant chemotherapy of primary breast cancer" Br J Cancer (2006) pp. 524-531, vol. 94, No. 4.
Massa, M. et al., "Circulating CD34+, CD133+, and vascular endothelial growth factor receptor 2-positive endothelial progenitor cells in myelofibrosis with myeloid metaplasia" J Clin Oncol (Aug. 2005) pp. 5688-5695, vol. 23, No. 24.
Richter-Ehrenstein, C. et al., "Endothelial progenitor cells in breast cancer patients" Breast Cancer Res Treat (2007) pp. 343-349, vol. 106.
Naik, R.P. et al., "Circulating endothelial progenitor cells correlate to stage in patients with invasive breast cancer" Breast Cancer Res Treat (2008) pp. 133-138, vol. 107.
Eisenhauer, E.A. et al., "New response evaluation criteria in solid tumours: revised RECIST guideline (version 1.1)" Eur J Cancer (2009) pp. 228-247, vol. 45.
Bertolini, F. et al., "The multifaceted circulating endothelial cell in cancer: towards marker and target identification" Nat Rev Cancer (2006) pp. 835-845, vol. 6.
Mancuso, P. et al., "Validation of a standardized method for enumerating circulating endothelial cells and progenitors: flow cytometry and molecular and ultrastructural analyses" Clin Cancer Res (Jan. 2009) pp. 267-273, vol. 15, No. 1.
Snaked, Y. et al., "Rapid chemotherapy-induced acute endothelial progenitor cell mobilization: implications for antiangiogenic drugs as chemosensitizing agents" Cancer Cell (Sep. 2008) pp. 263-273, vol. 14.
Farace, F. et al., "Vascular disrupting therapy-induced mobilization of circulating endothelial progenitor cells" Ann Oncol (Aug. 2007) pp. 1421-1422, vol. 18.
Khan, S.S. et al., "Detection of circulating endothelial cells and endothelial progenitor cells by flow cytometry" Cytometry B Clin Cytom (2005) pp. 1-8, vol. 64.
Bahlmann, F.H. et al., "Erythropoietin regulates endothelial progenitor cells" Blood (2004) pp. 921-926, vol. 103.
Friedrich, E.B. et al., "Role of extracellular signal regulated kinase for endothelial progenitor cell dysfunction in coronary artery disease" Basic Res Cardiol (2009) pp. 613-620, vol. 104.
Goss, G.D. et al., "Randomized, double-blind trial of carboplatin and paclitaxel with either daily oral cediranib or placebo in advanced non-small-cell lung cancer: NCIC clinical trials group BR24 study" J Clin Oncol (Jan. 2010) pp. 49-55, vol. 28, No. 1.
Spratlin, J.L. et al., "Phase I pharmacologic and biologic study of ramucirumab (IMC-1121B), a fully human immunoglobulin G1 monoclonal antibody targeting the vascular endothelial growth factor receptor-2" J Clin Oncol (Feb. 2010) pp. 780-787, vol. 28, No. 5.
Schwartz, J.D. et al., "Vascular endothelial growth factor receptor-1 in human cancer: concise review and rationale for development of IMC-18F1 (Human antibody targeting vascular endothelial growth factor receptor-1)" Cancer (Feb. 2010) pp. 1027-1032, vol. 116.
Jain, S. et al., "The effect of tetrathiomolybdate (TM) on circulating endothelial progenitor cells in women at moderate to high risk of breast cancer recurrence" Proc Breast Cancer Symp. (2010) pp. 1-2, Abstract 297.
Finney, L. et al., "X-ray fluorescence microscopy reveals large-scale relocalization and extracellular translocation of cellular copper during angiogenesis" Proc Natl Acad Sci USA (Feb. 2007) pp. 2247-2252.3, vol. 104, No. 7.
Dent, R. et al., "Triple-negative breast cancer: clinical features and patterns of recurrence" Clin Cancer Res. (Aug. 2007) pp. 4429-4434, vol. 13(15 Pt 1).
Folkman, J., "Angiogenesis in cancer, vascular, rheumatoid and other disease" Nat Med. (Jan. 1995) pp. 27-31, vol. 1, No. 1.
Gao, D. et al., "Endothelial progenitor cells control the angiogenic switch in mouse lung metastasis" Science (Jan. 2008) pp. 195-198, vol. 319, No. 5860.
Weidner, N. et al., "Tumor angiogenesis and metastasis-correlation in invasive breast cancer" N Engl J Med. (Jan. 1991) pp. 1-8, vol. 324, No. 1.
Iruela-Arispe, M. et al., "Angiogenesis: a dynamic balance of stimulators and inhibitors" Thromb Hemostasis (1997) pp. 672-677, vol. 78.
Badet, J. et al., "Specific binding of angiogenin to calf pulmonary artery endothelial cells" Proc Natl Acad Sci USA (1989) pp. 8427-8431, vol. 86.
Brem, S. et al., "Inhibition of angiogenesis and tumor growth in the brain: Suppression of endothelial cell turnover by penicillamine and depletion of copper, an angiogenic cofactor" Am J Pathol. (Nov. 1990) pp. 1121-1142, vol. 137, No. 5.
Juarez, J.C. et al., "Copper binding by tetrathiomolybdate attenuates angiogenesis and tumor cell proliferation through the inhibition of superoxide dismutase 1" Clin Cancer Res. (Aug. 2006) pp. 4974-4982, vol. 12, No. 16.
Hassouneh, B. et al., "Tetrathiomolybdate promotes tumor necrosis and prevents distant metastases by suppressing angiogenesis in head and neck cancer" Mol Cancer Ther. (Mar. 2007) pp. 1039-1045, vol. 6, No. 3.
Lowndes, S.A. et al., "The role of copper in tumour angiogenesis" J Mammary Gland Biol Neoplasia (Oct. 2005) pp. 299-310, vol. 10, No. 4.
Pan, Q. et al., "Copper deficiency induced by tetrathiomolybdate suppresses tumor growth and angiogenesis" Cancer Res. (Sep. 2002) pp. 4854-4859, vol. 62, No. 17.
Marttila-Ichihara, F. et al., "Vascular adhesion protein-1 enhances tumor growth by supporting recruitment of Gr-1+CD11b+ myeloid cells into tumors" Cancer Res. (Oct. 2009) pp. 7875-7883, vol. 69, No. 19.
Erler, J.T. et al., "Lysyl oxidase is essential for hypoxia-induced metastasis" Nature (Apr. 2006) pp. 1222-1226, vol. 440, No. 7088.
Alvarez, H.M. et al., "Tetrathiomolybdate inhibits copper trafficking proteins through metal cluster formation" Science (Jan. 2010) pp. 331-334, vol. 327, No. 5963.
Donate, F. et al., "Identification of biomarkers for the antiangiogenic and antitumour activity of the superoxide dismutase 1 (SOD1) inhibitor tetrathiomolybdate (ATN-224)" Br J Cancer (Feb. 2008) pp. 776-783, vol. 98, No. 4.
Jain, S. et al., "Incremental increase in VEGFR1+ hematopoietic progenitor cells and VEGFR2+ endothelial progenitor cells predicts relapse and lack of tumor response in breast cancer patients" Breast Cancer Research and Treatment (Feb. 2012) pp. 235-242, vol. 132, No. 1.
Brewer, G. et al., "Initial therapy of patients with Wilson's disease with tetrathiomolybdate" Arch Neurol. (Jan. 1991) pp. 42-47, vol. 48.

(56) References Cited

OTHER PUBLICATIONS

Kailajarvi, M. et al., "Early effects of adjuvant tamoxifen therapy on serum hormones, proteins and lipids" Anticancer Res. (Mar.-Apr. 2000) pp. 1323-1327, vol. 20, No. 2B.
Milde, F. et al., "The mouse retina in 3D: quantification of vascular growth and remodeling" Integrative Biology (2013) pp. 1426-1438, vol. 5.
Nowak, et al., "Circulating Endothelial Progenitor Cells are Increased in Human Lung Cancer and Correlate with Stage of Disease" European Journal of Cardio-thoracic Surgery (2010) pp. 758-763, vol. 37.
International Search Report dated May 31, 2012 issued in International Application No. PCT/US2012/026552.
Cheang, M.C. et al., "Gene expression profiling of breast cancer" Annu Rev Pathol (2008) pp. 67-97, vol. 3.
Shaked, Y. et al., "Rapid chemotherapy-induced acute endothelial progenitor cell mobilization: implications for antiangiogenic drugs as chemosensitizing agents" Cancer Cell (Sep. 2008) pp. 263-273, vol. 14.
Marttila-Ichihara, F. et al., "Vascular adhesion protein-1 enhances tumor growth by supporting recruitment of Gr-1$^+$CD11b$^+$ myeloid cells into tumors" Cancer Res. (Oct. 2009) pp. 7875-7883, vol. 69, No. 19.
Kaplan, R.N. et al., "VEGFR1-positive haematopoietic bone marrow progenitors initiate the pre-metastatic niche" Nature (Dec. 2005) pp. 820-827, vol. 438, No. 7069.
Erler, J.T. et al., "Hypoxia-induced lysyl oxidase is a critical mediator of bone marrow cell recruitment to form the premetastatic niche" Cancer Cell (Jan. 2009) pp. 35-44, vol. 15, No. 1.
Gao, D. et al., "Bone marrow-derived endothelial progenitor cells contribute to the angiogenic switch in tumor growth and metastatic progression" Biochim Biophys Acta. (Aug. 2009) pp. 33-40, vol. 1796, No. 1.
Gartner, E.M. et al., "A pilot trial of the anti-angiogenic copper lowering agent tetrathiomolybdate in combination with irinotecan, 5-flurouracil, and leucovorin for metastatic colorectal cancer" Invest New Drugs. (Apr. 2009) pp. 159-165, vol. 27, No. 2.

Brewer, G. et al., "Treatment of metastatic cancer with tetrathiomolybdate, an anticopper, antiangiogenic agent: Phase I study" Clin Ca Res. (Jan. 2000) pp. 1-11, vol. 6.
Redman, B. et al., "A phase II trial of TM in patients with advanced kidney cancer" Clin Ca Res. (May 2003) pp. 1666-16672, vol. 9.
Pass, H.I. et al., "A phase II trial of tetrathiomolybdate after surgery for malignant mesothelioma: final results" Ann Thorac Surg. (Aug. 2008) pp. 383-389, discussion 90, vol. 86, No. 2.
Jain, S. et al., "Incremental increase in VEGFR1$^+$ hematopoietic progenitor cells and VEGFR2$^+$ endothelial progenitor cells predicts relapse and lack of tumor response in breast cancer patients" Breast Cancer Research and Treatment (Feb. 2012) pp. 235-242, vol. 132, No. 1.
US Patent Application Publication No. US 2008/0003637 A1 published Jan.
Kaplan, R.N. et al., "Bone marrow cells in the 'pre-metastatic niche': within bone and beyond" Cancer Matastasis Rev (Dec. 2006) pp. 521-529, vol. 25, No. 4.
Bogos, K. et al., "High VEGFR-3-positive circulating lymphatic/vascular endothelial progenitor cell level is associated with poor prognosis in human small cell lung cancer" Clinical Cancer Research (2009) pp. 1741-1746, vol. 15, No. 5.
Le Bourhis, X. et al., "Role of endothelial progenitor cells in breast cancer angiogenesis: from fundamental research to clinical ramifications" Breast Cancer Research and Treatment (2010) pp. 17-24, vol. 120, No. 1.
Tilki, D. et al., "Emerging biology of vascular wall progenitor cells in health and disease" Trends in Molecular Medicine (2009) pp. 501-509, vol. 15, No. 11.
Farace, F. et al., "Levels of circulating CD45dimCD34+VEGFR2+ progenitor cells correlate with outcome in metastatic renal cell carcinoma patients treated with tyrosine kinase inhibitors" British Journal of Cancer (2011) pp. 1144-1150, vol. 104, No. 7.
European Search Report dated Dec. 23, 2014 issued in European Application No. EP 12749091.0.
European Communication dated Oct. 5, 2015 received from European Application No. 12 749 091.0.

\* cited by examiner

BONE MARROW-DERIVED HEMATOPOIETIC PROGENITOR CELLS AND ENDOTHELIAL PROGENITOR CELLS AS PROGNOSTIC INDICATORS FOR CANCER

CROSS-REFERENCE TO RELATED APPLICATIONS

This application claims priority to U.S. provisional application 61/446,296, filed Feb. 24, 2011, and U.S. provisional application 61/525,285, filed Aug. 19, 2011, each of which is incorporated herein by reference in its entirety.

BACKGROUND OF THE DISCLOSURE

Breast cancer remains the most commonly diagnosed cancer among women and the second leading cause of cancer mortality in the United States (Jemal A, et al., CA Cancer J Clin; 60: 277-300 (2010)). Despite major advances in adjuvant therapy for early-stage breast cancer, patients still have a 20 to 50% chance of relapse over 10 years (Brewster A M, et al., J Natl Cancer Inst; 100: 1179-83 (2008)). Metastasis, the final step of cancer progression, is responsible for most cancer related deaths and may occur after an extraordinarily long period of time after initial diagnosis and treatment (Chiang A C, et al., N Engl J Med; 359: 2814-23 (2008), Saphner T, et al., J Clin Oncol; 14: 2738-46 (1996)). Traditionally, probability of metastases has been correlated to tumor size and nodal status in breast cancer, but recent data suggest that molecular subtype may ultimately trump all traditional prognostic factors with the basal and HER2/neu intrinsic subtypes having the worst prognosis (Perou C M, et al., Nature; 406: 747-52 (2000), Sorlie T, et al., Proc Natl Acad Sci USA; 98: 10869-74 (2001), Sorlie T, et al., Proc Natl Acad Sci USA; 100: 8418-23 (2003), Cheang M C, et al., Annu Rev Pathol; 3: 67-97 (2008)). Though great strides have been made in delineating risk factors associated with recurrence, a reliable test to herald a clinical relapse does not exist. Several serum-based tumor markers are available in clinical practice for breast cancer, however a clinical intervention when a tumor marker becomes newly abnormal is usually too late to prevent an impending relapse. Therefore, American Society of Clinical Oncology (ASCO) guidelines do not recommend routine screening with tumor markers in adjuvant breast cancer patients (Harris L, et al., J Clin Oncol; 25: 5287-312 (2007)).

It is well established that tumor angiogenesis, the process of new blood vessel formation from preexisting vasculature, as well as differentiation and migration of endothelial cells, plays a crucial role in the growth and metastasis of tumors (Folkman J., N Engl J Med; 285: 1182-6 (1971), Carmeliet P, et al., Nature; 407: 249-57 (2000)). However less is known regarding the mechanisms that allow the transition from dormant, or occult, cancer cells to overt clinical relapse in cancer patients. Emerging evidence from preclinical models suggests that tumor-derived signals stimulate the quiescent bone marrow compartment, resulting in the expansion and mobilization of bone marrow-derived (BMD) VEGFR1$^+$ hematopoietic progenitor cells (HPCs) and VEGFR2$^+$ endothelial progenitor cells (EPCs), among others. HPCs home to the target organ and form clusters, or pre-metastatic niches, providing a permissive local microenvironment for the recruitment of incoming tumor cells and the establishment of micrometastases. EPCs are then recruited to the periphery of the micrometastatic lesions where they modulate the angiogenic switch, the transition from avascular micrometastatic lesions to vascularized macrometastatic disease. In these murine models, inhibition of VEGFR1$^+$ significantly reduces HPC localization to the premetastatic niche and development of metastasis. Similarly, blocking EPC mobilization strongly inhibits vasculogenesis and impairs the formation of macrometastases (Lyden D, et al., Nature Medicine; 7: 1194-201 (2001), Kaplan R N, et al., Nature; 438: 820-7 (2005), Gao D, et al., Science; 319: 195-8 (2008)).

The contribution of HPCs and EPCs to human cancer progression and pathogenesis is less well understood. HPCs have been implicated in defining the premetastatic niche in axillary lymph nodes of breast cancer patients and pelvic lymph nodes of prostate cancer patients (Kaplan R N, et al., Nature; 438: 820-7 (2005), Fujita K, et al., Cancer Sci; 100: 1047-50 (2009)). Elevated EPCs have been observed in cancer patients versus healthy controls (Taylor M, et al., Clin Cancer Res; 15: 4561-71 (2009)). EPCs have been also associated with advanced stage and worse prognosis in several hematologic and solid malignancies, and some but not all breast cancer studies (Gao D, et al., Trends Mol Med; 15: 333-43 (2009), Roodhart J M, et al., Biochim Biophys Acta; 1796: 41-9 (2009), Dome B, et al., Cancer Res; 66: 7341-7 (2006), Furstenberger G, et al., Br J Cancer; 94: 524-31 (2006), Massa M, et al., J Clin Oncol; 23: 5688-95 (2005), Richter-Ehrenstein C, et al., Breast Cancer Res Treat; 106: 343-9 (2007), Naik R P, et al., Breast Cancer Res Treat; 107: 133-8 (2008)).

It is well known that typical cancer therapeutic regimens, while effective in treating cancers, are associated with significant negative side effects. Therefore, for patients in remission or without active disease, treatment is discontinued or limited in use until progression or relapse of the cancer warrants further aggressive treatment. In patients at risk for future cancer progression or relapse, a biomarker that indicates imminent progression or relapse, while allowing sufficient time to treat the patient before progression or relapse occurs, would be highly desirable.

It is hypothesized that tumor recurrence results from residual, occult micrometastases that transition to macrometastases and become clinically detectable disease. Angiogenesis is fundamental to this process and preclinical models unequivocally demonstrate that an "angiogenic switch" must be activated to support tumor progression (Folkman J., Nat Med.; 1(1):27-31 (1995), Gao D, et al., Science.; 319(5860):195-8 (2008), Weidner N, et al., N Engl J Med.; 324:1-8 (1991), Iruela-Arispe M, et al., Thromb Hemostasis.; 78:672-7 (1997)). While there are many critical components of angiogenesis, copper is emerging as essential through experiments that demonstrate decreased endothelial cell proliferation, blood vessel formation and tumor growth with copper depletion (Badet J, et al., Proc Natl Acad Sci USA.; 86:8427-31 (1989), Brem S, et al., Am J Pathol.; 137:1121-42 (1990), Juarez J C, et al., Clin Cancer Res.; 12(16):4974-82 (2006), Hassouneh B, et al., Mol Cancer Ther.; 6(3):1039-45 (2007)). Copper appears to modulate angiogenesis through multiple mechanisms including NF-kB, HIF-1 alpha and by incorporation into copper-containing enzymes superoxide dismutase-1 (SOD1), vascular adhesion protein-1 (VAP-1) and lysyl oxidase (LOX) (11-14). Tetrathiomolybdate (TM), an oral copper chelator developed for treatment of Wilson's disease, blocks angiogenesis through inactivation of copper chaperones and decreased incorporation of copper into copper-containing enzymes (Alvarez H M, et al., Science.; 327(5963):331-4 (2010)). Copper may also play a role in migration and invasion as perinuclear copper is translocated to the leading edge of endothelial cell projections during angiogenesis (Finney L, et al., Proc Natl Acad Sci USA.; 104(7):2247-52.3 (2007)). Eventually, it is transported across the cell membrane into the extracellular space resulting in activation of proangiogenic cytokines and other molecules (Finney L, et al., Proc Natl Acad Sci USA.; 104(7):2247-52.3 (2007)). Copper chelators disrupt the organization of endothelial cells into new blood vessels by restricting the availability of extracellular copper to copper-containing enzymes critical for manufacture of a mature vascular structure (Finney L, et al., Proc Natl Acad Sci USA.; 104(7):2247-52.3 (2007)). Copper depletion in non-human primates decreases peripheral circulation of VEGFR2+ endothelial progenitor cells (EPCs), which are required for new blood vessel formation (Donate F, et al., Br J Cancer.; 98(4):776-83 (2008)). While VEGFR1+ hematopoietic progenitor cells (HPCs) and CD11b+ myeloid progenitor cells establish the premetastatic niche through remodeling of the extracellular matrix (Kaplan R N, et al., Nature.; 438(7069):820-7 (2005), Erler J T, et al., Cancer Cell.; 15(1):35-44 (2009)), colonization of the premetastatic niche by EPCs, among other cells, activates the angiogenic switch (Gao D, et al., Biochim Biophys Acta.; 1796(1):33-40 (2009)).

TM chelates copper via two distinct mechanisms. When given with food, it forms a stable complex with copper and protein and prevents absorption of copper from the gastrointestinal tract. When given between meals, it is absorbed into the blood where it binds to free copper and serum albumin. TM-bound copper is no longer available for cellular uptake and is slowly eliminated. Systemic copper depletion is measured through serum ceruloplasmin (Cp), the major extracellular copper transporter, since copper complexed with TM is detectable but not bioavailable (Gartner E M, et al., Invest New Drugs.; 27(2):159-65 (2009)). In initial phase I studies of advanced malignancy refractory to standard therapy, TM was well-tolerated and effective at inducing copper depletion with 15 of 40 patients maintaining stable disease for at least 90 days (Brewer G, Clin Ca Res.; 6:1-11 (2000)). A phase II study yielded stable disease for a median of 34.5 weeks in 13 patients with advanced renal cell carcinoma (Redman B, et al., Clin Ca Res.; 9:1666-16672 (2003)). Early-stage patients with malignant mesothelioma had a doubling of time to progression from 10 to 20 months after adjuvant TM (24). Although grade 3 or 4 hematologic toxicity occurred in up to 40% of patients, it was reversible and easily managed with dose reductions.

Several serum-based biomarkers, such as CEA and CA15-3, are currently in clinical use as indicators of cancer progression or relapse. Unfortunately, such markers herald relatively late-stage events in cancer progression, and cannot predict relapse sufficiently early in the metastatic process to enable treatment designed to halt further progression of disease. Therefore, there is an urgent need for improved methods to predict cancer progression, relapse, and response or resistance to cancer therapy, which will provide a sufficiently early signal that further treatments can be administered to prevent renewed metastasis and increased malignancy.

BRIEF SUMMARY OF THE DISCLOSURE

This disclosure provides methods of determining cancer progression or cancer relapse in a subject based on monitoring and detecting surges in the level of VEGFR1$^+$ hematopoietic progenitor cells (HPCs) and/or the level of VEGFR2$^+$ endothelial progenitor cells (EPCs).

In one aspect, the present method is based on measuring and monitoring the level of VEGFR1$^+$ hematopoietic progenitor cells (HPCs) and determining whether there is a surge in the level of HPCs. A surge in the level of HPCs indicates an increased risk of progression or relapse of cancer in the subject.

In another aspect, the level of VEGFR2$^+$CD133$^+$CD45$^{dim}$ endothelial progenitor cells (EPCs) is measured to determine if there is a surge in the levels of EPCs, which can also indicate an increased risk of progression or relapse of the subject's cancer.

Levels of HPCs and EPCs may be measured at the same time to determine whether there is a surge in HPCs or EPCs. Surges in HPCs and EPCs both indicate increased risk of progression or relapse, but the time frame in which the condition may manifest differs depending on whether a surge is seen in HPCs or EPCs. HPC surges occur earlier than EPC surges, relative to onset of progression or relapse. A surge in HPC levels indicates an increased risk of progression or relapse within one year, while a surge in EPC levels indicates that such events may occur within four months.

In another aspect, monitoring the levels of HPCs and EPCs is used in combination with cancer therapy to reduce the risk of cancer progression or relapse in a subject. If a surge in HPCs is detected, a cancer therapeutic that reduces the level or activity of HPCs can be administered to the subject. If a surge in EPCs is detected, a cancer therapeutic that reduces the level or activity of EPCs can be administered to the subject. Thus, the subject's risk of cancer progression or relapse is reduced.

In a further aspect, response or resistance of a subject's cancer to cancer treatment or therapy can be ascertained by measuring HPC and EPC levels in the subject during the course of treatment. A decline in HPC and/or EPC levels indicates that the subject's cancer is responding to the treatment. An increase in HPC and/or EPC levels indicates that the subject's cancer is resistant to the treatment.

This disclosure also provides a method of determining response or resistance to cancer treatment in a subject undergoing cancer treatment, the method including: obtaining a sample from said subject; measuring the level of VEGFR1$^+$CD45$^+$CD34$^+$ hematopoietic progenitor cells (HPCs) and the level of VEGFR2$^+$CD133$^+$CD45$^{dim}$ endothelial progenitor cells (EPCs) in said sample; repeating the steps of obtaining a sample from said subject and measuring the level of HPCs and EPCs at one or more later time points; and determining whether there is a decline or increase in the level of HPCs and/or EPCs in at least one later measurement, relative to an earlier measurement; wherein a decline in the level of HPCs and/or EPCs indicates that said subject's cancer is responding to cancer treatment, and wherein an increase in the level of HPCs and/or EPCs indicates that said subject's cancer is resistant to the cancer treatment.

BRIEF DESCRIPTION OF THE FIGURES

The patent or application file contains at least one drawing executed in color. Copies of this patent or patent application publication with color drawing(s) will be provided by the Office upon request and payment of the necessary fee.

Abbreviations: BC=breast cancer, NED=no evidence of disease, n=number of patients, t=number of treatment cycles, TM=tetrathiomolybdate, [a]=Patients may have had more than 1 response throughout study, [b]=1 patient rendered NED with therapy then relapsed, thereafter comprising the "relapsed" group, [c]=4 pts evaluable

DETAILED DESCRIPTION OF THE DISCLOSURE

Figure 1:
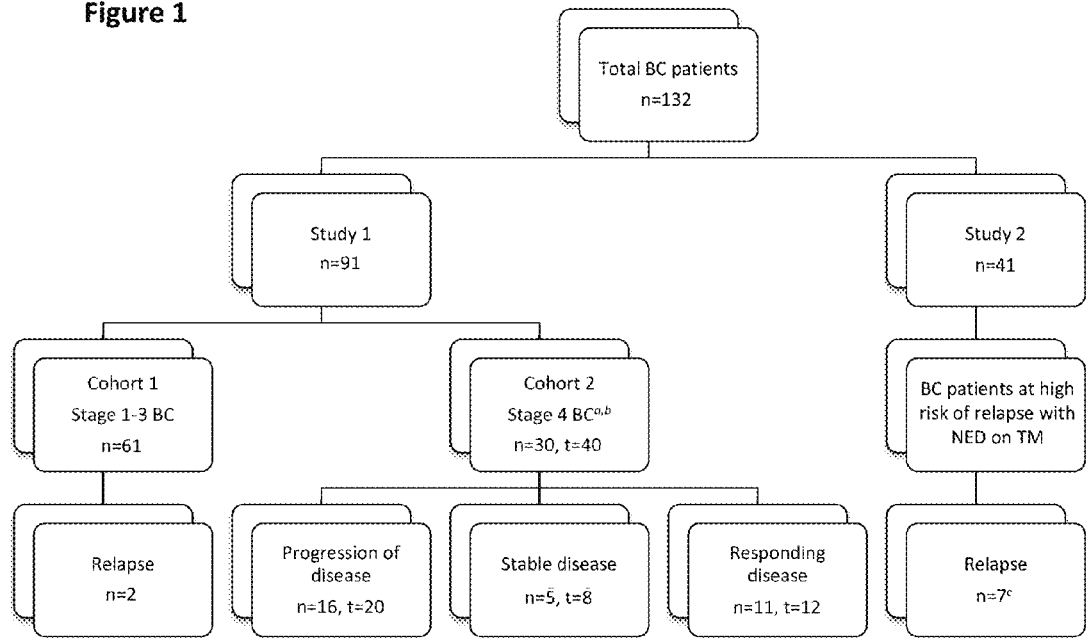
FIG. 1: This schema represents the 2 studies from which the observations are pooled. Study 1 contained 2 cohorts of breast cancer patients (stages 1 to 3 and metastatic patients) while Study 2 represents stage 2 to 4 breast cancer patients without evidence of disease but at high risk of relapse.

Advances in cancer treatments have added years to the lives of many cancer patients. However, ongoing and often expensive monitoring of cancer patients whose cancer is in remission, or whose cancer is not progressing, can only inform when a patient's cancer has finally progressed or relapsed, at which point the cancer has typically become much more aggressive and difficult to treat. A method of diagnosing early predictors of cancer progression, at a sufficiently early point that such impending relapse or progression can be prevented, would be of tremendous benefit to cancer patients and diagnosticians.

Thus far, such early predicting factors have remained elusive. However, the inventors have herein identified circulating cell types that are demonstrably associated with impending cancer development. Appearance of increased numbers of these cells in the circulation signals the start of physiological events that culminate in cancer relapse or progression. Identification of such "early warning" cells, specifically VEGFR1$^+$ hematopoietic progenitor cells (HPCs) and VEGFR2$^+$ endothelial progenitor cells (EPCs), provides a novel diagnostic biomarker for cancer progression or relapse. Identifying increases in HPCs and EPCs is further useful for optimizing treatment regimes for cancer patients in remission, by providing information on cellular events leading to cancer development which can be prevented or slowed by administration of appropriate treatments. Further, measurements of HPCs and EPCs can identify whether a patient's cancer is responding or resistant to treatment with cancer therapeutics.

Based on the preclinical data characterizing the angiogenic switch in murine model systems, the inventors designed a study to characterize the angiogenic switch in a cancer population. From an analysis of the temporal relationship of HPCs and EPCs in cancer patients, the inventors have found a predictable relationship of increases in HPCs, followed by increases in EPCs, heralding impending relapse of cancer in patients. Furthermore, the inventors have determined that quantitative changes in these cells could also predict response or resistance to therapy in cancer patients receiving systemic therapy for advanced disease, which leads to progression of cancer in such patients.

Therefore, in one aspect, this disclosure provides a method of determining the risk of cancer progression or cancer relapse in a subject based on measuring the level of VEGFR1$^+$ hematopoietic progenitor cells (HPCs) in the subject, wherein said sample, wherein a surge in the level of HPCs indicates an increased risk of cancer relapse or cancer progression in the subject.

In a specific embodiment, the HPCs are characterized as VEGFR1$^+$CD45$^+$CD34$^+$.

In another embodiment, as an additional step in a method of determining the risk of cancer progression or cancer relapse, the level of VEGFR2$^+$ endothelial progenitor cells (EPCs) is also measured in addition to measuring the level of VEGFR1$^+$ HPCs, wherein a surge in the level of EPCs indicates an increased risk of imminent progression or relapse of cancer in the subject.

In a specific embodiment, the EPCs are characterized as VEGFR2$^+$CD133$^+$CD45$^{dim}$.

In a further aspect, this disclosure provides a method of determining the risk of cancer progression or cancer relapse in a subject based on measuring the level of VEGFR2$^+$ endothelial progenitor cells (EPCs) in the subject, wherein a surge in the level of EPCs indicates an increased risk of cancer progression or relapse in the subject.

In a specific embodiment, the EPCs are characterized as VEGFR2$^+$CD133$^+$CD45$^{dim}$.

The phrase "CD45$^{dim}$" is understood by the skilled artisan and refers to cells that express the CD45 marker, but at a much reduced intensity, which can be determined in, e.g., a fluorescence-activated cell sorting (FACS) analysis, relative to CD45$^+$ cells (also referred to as "CD45 bright" cells) such as monocytes and HPCs. EPCs (also referred to in the art as Circulating Endothelial Progenitor cells or CEPs) are postulated to contribute to angiogenesis and to assist in nascent vessel formation (Bertolini et al., *Nat Rev Canc.* 6:835-45 (2006); Yoder et al., *Blood* 109:1801-9 (2007)). EPCs are less mature than Circulating Endothelial Cells (CECs) which are CD45$^-$. Therefore, EPCs are associated with early angiogenic events, as opposed to CECs which represent a more mature phenotype and are associated with later events in angiogenesis.

The methods of the invention include measuring levels of HPCs and EPCs and determining surges or declines in cell numbers as predictive measures. As used herein, a "surge" indicates a marked increase in the level of relevant cells, typically from one measurement to one or more later measurements. In other instances, an increase in the level of relevant cells can be determined from one measure in a subject of interest relative to control (e.g., a value or a range of values for normal, i.e., healthy, individuals). Surges may be a two-fold increase in cell levels (i.e., a doubling of cell counts), a three-fold increase in cell levels (i.e., a tripling of cell numbers), a four-fold increase in cell levels (i.e., an increase by four times the number of cells in a previous measurement), or a five-fold or greater increase. In addition to the marked increase described as a surge, lesser increases in the levels of relevant cells also have relevance to the methods of the invention. Increases in cell levels may be described in terms of percentages. Surges may also be described in terms of percentages. For example, a surge or increase may be an increase in cell levels of 10%, 20%, 30%, 40%, 50%, 60%, 70%, 80%, 90%, or 100% or more. A "decline" indicates a decrease from one measurement to one or more later measurements. A decline may be a 5%, 10%, 15%, 20%, 25%, 30%, 35%, 40%, 45%, 50%, 55%, 60%, 65%, 70%, 75%, 80%, or 85% or greater decrease in cell levels from one measurement to one or more later measurements.

To measure the levels of HPCs and EPCs in a subject, a biological sample can be taken from the subject, which can be a sample of sputum, cerebrospinal fluid, blood, blood fractions such as serum and plasma, blood cells (e.g., white cells), tissue or fine needle biopsy samples, urine, peritoneal fluid, and pleural fluid, or cells there from. The term "tissue" as used herein refers to cellular material from a particular physiological region. The cells in a particular tissue can include several different cell types. A non-limiting example of this would be tumor tissue that includes endothelial cells and blood cells, all contained in a given tissue section or sample. It will be appreciated from the invention that in addition to solid tissues, the term "tissue" is also intended to encompass non-solid tissues, such as blood. In a specific embodiment, the sample is a blood sample.

The sample is subjected to analysis to determine the numbers of HPCs and EPCs relative to total numbers of lymphocytes in the sample. Analysis may include contacting a sample with one or more antibodies selective for HPC and/or EPC cell surface markers; separating or quantifying cells based on binding to such antibodies; and determining the fraction of cells that bind to the antibodies. The method may be carried out in a device adapted to separate or quantify cells on the basis of antibody binding, and further wherein said device is programmed to provide a report that identifies the fraction of HPCs and/or EPCs that bind to the antibodies. The device may be fluorescence-activated cell sorting (FACS). Cell measurements may be carried out for example, by immunoassays including, but not limited to, western blots, immunohistochemistry, immunocytochemistry, in situ hybridization, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, immunofluorescence, or flow cytometry. Alternatively, the detecting may include detecting or quantifying HPC and/or EPC mRNA, e.g., via real-time PCR.

HPCs and EPCs can be identified by FACS analysis using the gating strategies as provided in Example 1 and FIGS. 5A-5C and 6A-6C.

Samples are obtained from a subject as determined by a physician. Samples may be obtained once every week, every two weeks, every four weeks, every six weeks, every month, every two months, every three months, or every four months or more. Samples may be obtained every four to six weeks, every one to two months, every one to three months, every one to four months, or every two to four months apart.

The term "cancer" refers to a class of diseases in which a group of cells display uncontrolled growth, invasion, and metastasis. The term is meant to include, but not limited to, a cancer of the breast, respiratory tract, brain, reproductive organs, digestive tract, urinary tract, eye, liver, skin, head and neck, thyroid, and parathyroid. The cancer may be a solid tumor, a non-solid tumor, or a distant metastasis of a tumor. Some specific examples of cancers include, but are not limited to, leukemias; lymphomas; multiple myelomas; bone and connective tissue sarcomas; brain tumors; breast cancer; adrenal cancer; thyroid cancer; pancreatic cancer; pituitary cancers; eye cancers; vaginal cancers; cervical cancers; uterine cancers; ovarian cancers; esophageal cancers; stomach cancers; colon cancers; rectal cancers; gastric cancers; liver cancers; bladder cancers; gallbladder cancers; cholangiocarcinomas; lung cancers; testicular cancers; prostate cancers; penile cancers; oral cancers; basal cancers; salivary gland cancers; pharynx cancers; skin cancers; kidney cancers; and Wilms' tumor. Examples of solid tumors include solid tumors of the breast, prostate, colon, pancreas, lung, gastric system, bladder, and bone/connective tissue.

As used herein, "relapse" or "recurrence" is defined as the appearance of one or more new tumor lesions in a subject who previously had cancer but has had no overt evidence of cancer as a result of surgery and/or therapy until relapse. Such recurrence of cancer cells can be local, occurring in the same area as one or more previous tumor lesions, or distant, occurring in a previously lesion-free area such as lymph nodes or other areas of the body.

Progression, response to treatment, and resistance to treatment are defined according to RECIST guidelines (Eisenhauer et al., *Eur J Cancer* 45:228-247, 2009, incorporated herein by reference in entirety). For patients with measurable disease, defined as the presence of at least one measurable lesion ("target lesion") as described in the RECIST guidelines, an initial assessment of tumor lesions/ lymph nodes, to determine overall tumor burden at baseline, is used to determine future response or progression.

"Response to treatment" includes complete response and partial response to treatment. "Complete response" (CR) is defined as the disappearance of all target lesions and non-target lesions and normalization of tumor marker levels. "Partial response" (PR) is defined as an at least 30% decrease in the sum of the diameters of target lesions. Therefore, "response to treatment" includes an at least 30%-100% decrease in the sum of the diameters of target lesions, or disappearance of all target lesions and non-target lesions and normalization of tumor marker levels. "Progression" or "progressive disease" (PD) is defined as an at least 20% increase in the sum of the diameters of target lesions, progression (increase in size) of any existing non-target lesions, and is also determined upon appearance of one or more new lesions. Non-CR/non-PD is identified by the persistence of one or more non-target lesions and/or maintenance of above-normal tumor marker levels. "Stable disease" (SD) is defined as an insufficient increase to qualify for PD, but an insufficient decrease to qualify for PR.

The subject or patient can be any mammal, including a human. In particular, the subject can be a mammal who previously had cancer but appears to have recovered as a result of surgery and/or therapy, or who presently has cancer and is undergoing cancer therapy, or has completed a cancer therapeutic regime, or has received no cancer therapy.

In accordance with this disclosure, in a subject who previously had cancer but appears to have recovered, a surge in HPCs detected in such subject indicates an increased risk or probability of cancer relapse within one year, or within 11, 10, 9, 8, 7, 6, 5, 4, or 3 months, often within four to eight months. Increased risk is compared to a subject (e.g., same subject) without a surge in HPCs. Similarly, in a subject who presently has cancer, a surge in HPCs detected in such subject indicates an increased risk or probability of cancer progression within one year, often within four to eight months. This allows a window of opportunity for treatment to prevent the progression or relapse of the subject's cancer, before the progression or relapse occurs. Without being bound, it is thought that an increase in HPCs primes tissues for future tumor development by creating "niche" areas for tumor growth, thus a surge in the levels of HPCs signals the start of tumorigenic events before tumor growth or re-growth happens.

Further according to this disclosure, in a subject who previously had cancer but appears to have recovered, a surge in EPCs detected in such subject indicates an increased risk or probability that relapse will occur within three to five months, often within one, two or three months. Increased risk is compared to a subject (e.g., same subject) without a surge in EPCs. Similarly, in a subject who presently has cancer, a surge in EPCs detected in such subject indicates an increased risk or probability of cancer progression within three to five months, often within one, two or three months. "Imminent progression or relapse" is thus defined as progression or relapse of said subject's cancer within three to five months, typically within one, two, or three months. Thus, a surge in EPCs indicates that cancer progression or relapse is imminent, and aggressive treatment to halt such progression or relapse is warranted. Without being bound, it is thought that an increase in EPCs signals increased angiogenic development required for tumor formation.

The inventors have further determined that surges in HPCs and/or EPCs in a sample from a subject undergoing cancer therapeutic treatment, relative to measurements of HPCs and EPCs in a sample from that subject at an earlier time point, indicates that the subject's cancer is resistant to treatment, and the patient is at increased risk for cancer progression, relative to a subject who does not show surges in HPCs and/or EPCs in his or her patient samples over time while undergoing treatment. Similarly, the inventors have determined that declines in the levels of HPCs and/or EPCs in a patient sample, relative to measurements of HPCs and EPCs from a patient sample at an earlier time point, indicates that said subject's cancer is responding to the treatment, and that subject's risk for progression is reduced relative to a subject who does not show a decline in the levels of HPCs and/or EPCs in his or her patient samples over time while undergoing treatment.

Therefore, in another embodiment, this disclosure provides a method of determining response or resistance to cancer treatment in a subject undergoing cancer treatment, based on measuring the level of $VEGFR1^+CD45^+CD34^+$ hematopoietic progenitor cells (HPCs) and the level of $VEGFR2^+CD133^+CD45^{dim}$ endothelial progenitor cells (EPCs) in the subject, and determining whether there is a decline or surge in the level of HPCs and/or EPCs. A decline in the level of HPCs and/or EPCs indicates that the subject is responding to cancer treatment, and a surge in the level of HPCs and/or EPCs indicates that the subject is resistant to the cancer treatment.

In still another embodiment, this disclosure provides methods to determine the risk of cancer progression in a subject who has cancer, by measuring the level of $VEGFR1^+CD45^+CD34^+$ hematopoietic progenitor cells (HPCs) and the level of $VEGFR2^+CD133^+CD45^{dim}$ endothelial progenitor cells (EPCs) in the subject, and determining whether there is a surge in the level of HPCs and/or EPCs in at least one later measurement, relative to an earlier measurement. A surge in the level of HPCs and/or EPCs indicates an increased risk of cancer progression.

Because the surges of HPCs and EPCs have been identified as "early warnings" for cancer progression or relapse, monitoring the levels of these cells provides an important basis of optimizing treatment regimes.

The terms "treatment", "treating", and the like, as used herein include amelioration or elimination of a developed disease or condition once it has been established or alleviation of the characteristic symptoms of such disease or condition. As used herein these terms also encompass, depending on the condition of the subject, preventing the onset of a disease or condition or of symptoms associated with a disease or condition, including reducing the severity of a disease or condition or symptoms associated therewith prior to affliction with said disease or condition. Such prevention or reduction prior to affliction refers to administration of one or more cancer therapeutics to a subject that is not at the time of administration afflicted with the disease or condition. "Preventing" also encompasses preventing the recurrence or relapse of a previously existing disease or condition or of symptoms associated therewith, for instance after a period of improvement.

For example, the level of $VEGFR1^+CD45^+CD34^+$ hematopoietic progenitor cells (HPCs) and the level of $VEGFR2^+CD133^+CD45^{dim}$ endothelial progenitor cells (EPCs) can be monitored in patients who appear to have recovered from cancer as well as patients who presently have cancer. In accordance with this disclosure, to prevent relapse or cancer progression, an optimal time to administer a cancer therapeutic that reduces the level or activity of HPCs is indicated once a surge in the level of HPCs is detected, and wherein an optimal time to administer a cancer therapeutic that reduces the level or activity of EPCs and/or cancer cells is indicated once a surge in the level of EPCs is detected. In some embodiments, a cancer therapeutic is administered to a patient once a surge in the level of HPCs has been detected, and a surge in the level of EPCs has not been detected.

The term "cancer treatment" refers to any treatment that reduces levels, function or activity of HPCs, EPCs, and/or cancer cells and/or causes destruction of such cells. Cancer treatment includes administration of any cancer agent including radioactive isotopes, chemotherapeutic agents, and toxins such as small molecule toxins or enzymatically active toxins of bacterial, fungal, plant or animal origin, including fragments and/or variants thereof. Examples of cytotoxic agents include, but are not limited to maytansinoids, yttrium, bismuth, ricin, ricin A-chain, doxorubicin, daunorubicin, taxol, ethidium bromide, mitomycin, etoposide, tenoposide, vincristine, vinblastine, colchicine, dihydroxy anthracin dione, actinomycin, diphtheria toxin, Pseudomonas exotoxin (PE) A, PE40, abrin, abrin A chain, modeccin A chain, alpha-sarcin, gelonin, mitogellin, retstrictocin, phenomycin, enomycin, curicin, crotin, calicheamicin, sapaonaria officinalis inhibitor, and glucocorticoid and other chemotherapeutic agents, as well as radioisotopes. Cancer treatment further includes removal of cancerous tissue or cells by surgery, biopsy, or other means.

The recommended dosages of the cancer agents currently used for the prevention, treatment, and/or management of cancer can be obtained from any reference in the art including, but not limited to, Hardman et al., eds., Goodman & Gilman's *The Pharmacological Basis Of Therapeutics,* 10th ed, Mc-Graw-Hill, N.Y., 2001; and *Physician's Desk Reference* (60$^{th}$ ed., 2006), which are incorporated herein by reference in their entirety.

This disclosure further encompasses administration of one or more antagonists that inhibit HPCs, EPCs, and/or cancer cells as a cancer treatment. An "antagonist" reduces activity or function of a protein and/or cell. For example, a compound can act as an antagonist by inhibiting, reducing or eliminating protein expression, or preventing protein activity, or preventing the interaction of a protein with other proteins, resulting in an inhibition of a protein-mediated function or signaling, any of which can inhibit activity or function of a cell. Examples of antagonists include peptides, polypeptides, proteins, antibodies, antisense oligonucleotides, RNAi/siRNA, small molecules, chemotherapeutic agents, and fragments, derivatives and analogs thereof, that inhibit the activity or function of HPCs, EPCs, and/or cancer cells. For example, an antagonist of VEGFR1 can inhibit activity or function of HPCs, while an antagonist of VEGFR2 can inhibit activity or function of EPCs.

Preferred treatments reduce the level or activity of HPCs and/or EPCs.

Antagonists of HPCs and EPCs include antibody therapeutics marketed under the name cediranib (AZD2171/ Recentin®; AstraZeneca), sunitinib (Sutent®; Pfizer), axitinib (Inlyta®; Pfizer), pazopanib (Votrient®; GlaxoSmithKline), and bevacizumab (Avastin®; Genentech). HPC/EPC antagonists also include macrophage inflammatory protein 1-alpha (MIP-1-alpha) and LD78 (see U.S. Pat. No. 5,856,301), the alpha globin chain of hemoglobin and beta globin chain of hemoglobin (see U.S. Pat. No. 6,022,848), interferon gamma (see U.S. Pat. No. 5,807,744), recombinant-methionyl human G-CSF (Neupogen®, Filgastim; Amgen), GM-CSF (Leukine™, Sargramostim; Immunex), erythropoietin (rhEPO, Epogen®; Amgen), thrombopoietin (rhTPO; Genentech), interleukin-11 (rhIL-11, Neumega™; American Home Products), Flt3 ligand (Mobista; Immunex), multilineage hematopoietic factor (MARstem™; Maret Pharm.), myelopoietin (Leridistem; Searle), IL-3, myeloid progenitor inhibitory factor-1 (Mirostipen; Human Genome Sciences), stem cell factor (rhSCF, Stemgen®; Amgen), and CDK4/6 inhibitors.

HPC antagonists include anti-VEGF antibodies and anti-VEGFR1 antibodies.

EPC antagonists include anti-VEGFR2 antibodies such as sorafenib (Nexavar™; Bayer). A preferred anti-angiogenic agent that antagonizes EPC activity is tetrathiomolybdate (TM), an oral copper chelator. TM and other copper chelators decrease peripheral circulation of EPCs and prevent angiogenesis.

Cancer agents, including antagonists of HPCs, EPCs, and/or cancer cells, can be administered to a subject in a therapeutically effective amount.

As used herein, the terms "therapeutically effective amount" and "effective amount" are used interchangeably to refer to an amount of a composition of the invention that is sufficient to result in the prevention of the development, recurrence, or onset of cancer stem cells or cancer and one or more symptoms thereof, to enhance or improve the prophylactic effect(s) of another therapy, reduce the severity and duration of cancer, ameliorate one or more symptoms of cancer, prevent the advancement of cancer, cause regression of cancer, and/or enhance or improve the therapeutic effect(s) of additional anticancer treatment(s).

A therapeutically effective amount can be administered to a patient in one or more doses sufficient to palliate, ameliorate, stabilize, reverse or slow the progression of the disease, or otherwise reduce the pathological consequences of the disease, or reduce the symptoms of the disease. The amelioration or reduction need not be permanent, but may be for a period of time ranging from at least one hour, at least one day, or at least one week or more. The effective amount is generally determined by the physician on a case-by-case basis and is within the skill of one in the art. Several factors are typically taken into account when determining an appropriate dosage to achieve an effective amount. These factors include age, sex and weight of the patient, the condition being treated, the severity of the condition, as well as the route of administration, dosage form and regimen and the desired result.

If a cancer treatment is determined to be ineffective, as evidenced by a surge in HPCs and/or EPCs during the course of treatment, alternative treatment, for example a different type of agent, may then be administered to the subject in hopes of achieving a better outcome.

The invention is further illustrated by the following non-limiting examples.

EXAMPLES

Example 1—HPC and EPC Surges Predict Cancer Progression

Patients with breast cancer were enrolled on one of two Institutional Review Board approved studies at Weill Cornell Medical College (WCMC) Iris Cantor Breast Cancer Center. Written informed consent was obtained in accordance with the Declaration of Helsinki.

Study Population and Design

Study 1:

Patients with pathologically confirmed stage 1 to 4 invasive breast cancer were recruited from WCMC Iris Cantor Breast Cancer Center from March 2005 to July 2009 and divided into 2 cohorts:

Cohort 1:

Patients with stage 1 to 3 breast cancer were enrolled following definitive surgery (lumpectomy and axillary evaluation or mastectomy) and prior to the initiation of adjuvant systemic therapy. Adjuvant systemic therapy was based on physician's choice and could consist of the following: chemotherapy, hormonal therapy, biologic and/or radiation therapy. Clinical specimens were obtained at the initiation of systemic therapy, halfway through systemic chemotherapy and every three months at routine follow-up thereafter.

Cohort 2:

Patients with stage 4 breast cancer with established metastasis or with presentation of newly diagnosed stage 4 disease (de novo stage 4 breast cancer) were enrolled upon starting a new systemic therapy. Clinical specimens were obtained monthly and coincident with an imaging scan to assess response to therapy.

Study 2:

Patients without evidence of breast cancer but at high risk of relapse with pathologically confirmed stage 2 or greater triple-negative breast cancer and any subtype of stage 3 or stage 4 breast cancer with no evidence of disease (stage 4 NED) were enrolled on a phase II trial of tetrathiomolybdate (TM), a copper depletion compound at WCMC Iris Cantor Breast Cancer Center (NCT00195091, 0903-882) from July 2007 to June 2010. In this trial, clinical specimens were obtained on a monthly basis for up to two years.

Clinical Response

Response was based on Response Evaluation Criteria in Solid Tumors (RECIST) (Eisenhauer E A, et al., Eur J Cancer; 45: 228-47 (2009)). Patients with progressive disease (PD) comprised the "progression of disease" group. Patients with complete response (CR) or partial response (PR) comprised the "responding disease" group. Patients with stable disease (SD) comprised the "stable disease" group.

HPC and EPC Quantitation

Blood samples were obtained prior to chemotherapy administration. Ten to 20 mL of venous blood were collected in EDTA-containing tubes and processed within 12 hours. Laboratory evaluation of specimens in both studies was identical. Peripheral blood mononuclear cells were isolated by Ficoll density-gradient centrifugation. To quantitate circulating EPCs, cells were stained with CD133-PE (Miltenyi Biotec, Auburn, Calif.), VEGFR2-APC (R&D Systems, Minneapolis, Minn.), and CD45-PerCP (BD Biosciences, Franklin Lakes, N.J.). To quantitate HPCs, cells were stained with CD34-FITC (BD Biosciences), VEGFR1-APC (R&D Systems), and CD45-PerCP (BD Biosciences). An aliquot of cells was also stained with the appropriate isotype controls (mouse anti-human IgG1k). Samples were analyzed using a FACSCalibur flow cytometer (Bectin Dickinson, San Jose, Calif.). Three hundred thousand events were collected in the nucleated cell gate (excludes debris and platelets). Data analysis was done using FlowJo software (FlowJo, Ashland, Oreg.). A series of consecutive gates were made to include and exclude acquired events to quantitate specific populations such as $CD45^+$, $CD34^+$, $VEGFR1^+$. The number of EPCs and HPCs per mL of blood was calculated as follows: HPC/mL=(# HPC events/# lymphocyte events)×absolute lymphocyte count (lymphocytes/mL). EPC/mL=(# EPC events/# lymphocyte events)×absolute lymphocyte count (lymphocytes/mL).

Definition of HPCs and EPCs

The definition of HPCs and EPCs was based on the identified phenotypes (Bertolini F, et al., Nat Rev Cancer; 6:835-45 (2006); Mancuso P, et al., Clin Cancer Res; 15: 267-73 (2009)). HPCs were defined as $CD45^+$, $CD34^+$, $VEGFR1^+$. EPCs were defined as $CD45^{dim}$, $CD133^+$, $VEGFR2^+$.

Hematopoietic Progenitor Cell ($CD34^+$/$CD45^+$/$VEGFR1^+$) Enumeration:

(See FIGS. 5A-5C) (A) The R1 gate was used to select the nucleated cell events, and the R2 gate was used to select lymphocyte events. (B) The R2 gate was used to select $CD34^+$, $CD45^+$ events from the R1 gate. (C) Quadrant gates were used to identify $VEGFR1^+$ events from the R3 gate: isotype control (upper panel) was used to accurately place the quadrant gate for CD34, VEGFR1 stained cells (lower panel). The absolute number of HPC's per mL of blood was calculated by multiplying the number of HPC events collected by a ratio of the absolute lymphocyte count/mL of the blood sample to the number of lymphocytes (determined by the R2 gating) in the collected data (HPC/mL=absolute lumphocyte count/mL×HPC events/number of events in lymphocyte gate).

Endothelial Progenitor Cell ($CD45^{dim}$/$CD133^+$/$VEGFR2^+$) Enumeration.

(See FIGS. 6A-6C) (A) The R1 gate was used to select nucleated cell events, and the R2 gate was used to select lymphocyte events. (B) The R3 gate was used to select $CD45^{dim}$ events from the R1 gate. (C) Quadrant gates were used to identify $CD133^+$, $VEGFR2^+$ events from the R3 gate: isotype control (upper panel) was used to accurately place the quadrant gate for the VEGFR2, CD133 stained cells (lower panel). The absolute number of EPC's per mL of blood was calculated by multiplying the number of EPC events collected by a ratio of the absolute lymphocyte count/mL of the blood sample to the number of lymphocytes (determined by the R2 gating) in the collected data (EPC/mL=absolute lymphocyte count/mL×EPC events/number of events in lymphocyte gate).

Statistical Analysis

All analyses were performed in GraphPad Prism Version 5.0 (GraphPad Software, La Jolla, Calif.). Results were expressed as medians and range. In metastatic patients, baseline was defined as initiation of a new systemic therapy, and comparisons between baseline and post-response HPC and EPC values were made with the Wilcoxon signed-rank test. Comparisons between baseline and post-response absolute lymphocyte values were made with standard paired t test. In the patients who relapsed from a prior no evidence of disease state, baseline was defined as median of EPC and HPC values prior to EPC or HPC surge, and comparisons between baseline and "prior to relapse" were made with the Wilcoxon signed-rank test. All P values were two-sided with statistical significance evaluated at the 0.05 alpha level.

Results:

One hundred thirty-two patients were enrolled on two studies, FIG. 1. Data from both studies were combined to analyze patients who entered the study without overt breast cancer and developed recurrence while on study ("relapsed group": Study 1 [observational study]/Cohort 1 and Study 2 [TM trial]). Patients with stage 4 breast cancer were grouped according to response by RECIST (Study 1/Cohort 2). Demographic variables are shown in Table I.

TABLE I

Patient characteristics at study entry.

|  | Study 1 | Study 2 | Pooled |
| --- | --- | --- | --- |
| Total patients, n | 91 | 41 | 132 |
| Median age, y (range) | 48 (26-74) | 51 (29-66) | 49 (26-74) |
| Stage 1, n (%) | 16 (17.6%) | 0 (0%) | 16 (12.1%) |
| Stage 2, n (%) | 24 (26.4%) | 3 (7.3%) | 27 (20.5%) |
| Stage 3, n (%) | 21 (23.1%) | 26 (63.4%) | 47 (35.6%) |
| Stage 4, n (%) | 30 (33.0%) | 12 (29.2%) | 42 (31.8%) |
| De novo, n | 8 | 0 | 8 |
| Established metastasis, n | 22 | 0 | 22 |
| No evidence of disease, n | 0 | 12 | 12 |
| Adjuvant patients, n | 61 | 29 | 90 |

TABLE I-continued

Patient characteristics at study entry.

|  | Study 1 | Study 2 | Pooled |
|---|---|---|---|
| Chemotherapy | 60 | 28 | 88 |
| Anthracycline only | 3 | 1 | 4 |
| Anthracycline and taxane | 25 | 27 | 52 |
| Chemo and trastuzumab | 21 | 5 | 26 |
| Metastatic patients, n | 30 | 12 | 42 |
| Median chemo regimens, n (range) | 2 (0-6) | 1 (0-3) | 1 (0-6) |
| Taxanes | 22 | 6 | 28 |
| Vinorelbine | 9 | 0 | 9 |
| Gemcitabine | 6 | 0 | 6 |

TABLE I-continued

Patient characteristics at study entry.

|  | Study 1 | Study 2 | Pooled |
|---|---|---|---|
| Capecitabine | 22 | 2 | 24 |
| Ixabepilone | 8 | 0 | 8 |
| Median hormone regimens, n (range) | 1 (0-4) | 1 (0-4) | 1 (0-4) |
| Median biologics, n (range) | 0 (0-2) | 0 (0-1) | 0 (0-2) |

Of the 102 patients who at study entry were without evidence of disease by physical examination, laboratory data, tumor markers or imaging, 10 patients developed overt breast cancer recurrence while on study. Three patients relapsed 1 to 2 months after study entry and were not included in the analysis. Of the seven evaluable patients, 3 were from Study 1 and 4 from Study 2. Four patients had stage 4 breast cancer without any evidence of disease (2 were estrogen receptor [ER] positive, 1 was HER2/neu positive, 1 was triple-negative), 2 patients had a prior diagnosis of stage 3C breast cancer (ER-positive and triple-negative) and 1 patient had a prior diagnosis of stage 2 breast cancer (triple-negative). The median primary tumor size was 3 cm (range 1.7 to 4.3 cm) and number of positive lymph nodes involved was 1 (range 1 to 42).

Figure 2:
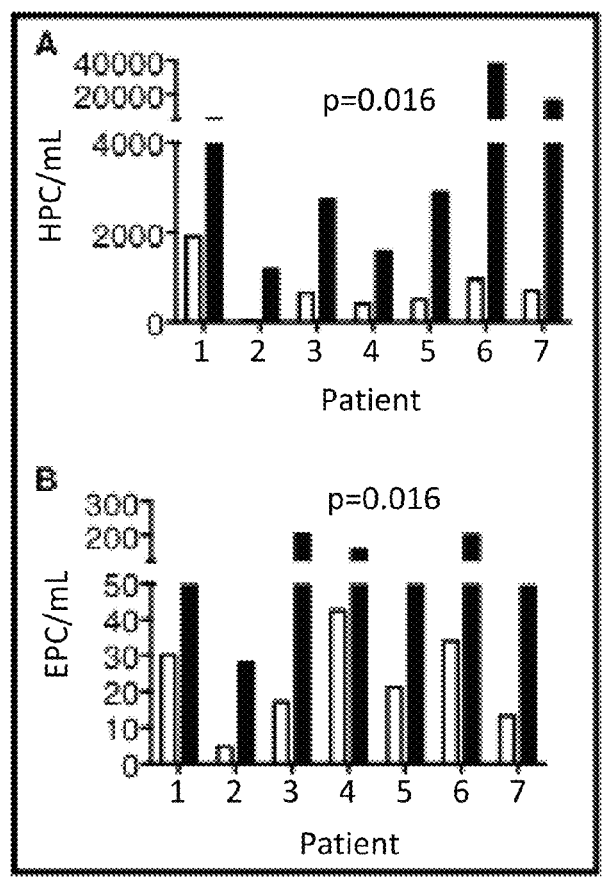
FIGS. 2A-2B: Surge in (A) VEGFR1$^+$ HPCs and (B) VEGFR2$^+$ EPCs is observed from baseline (white bar) immediately prior to relapse (black bar) in 7 breast cancer patients without evidence of disease at study entry.
Figure 3:
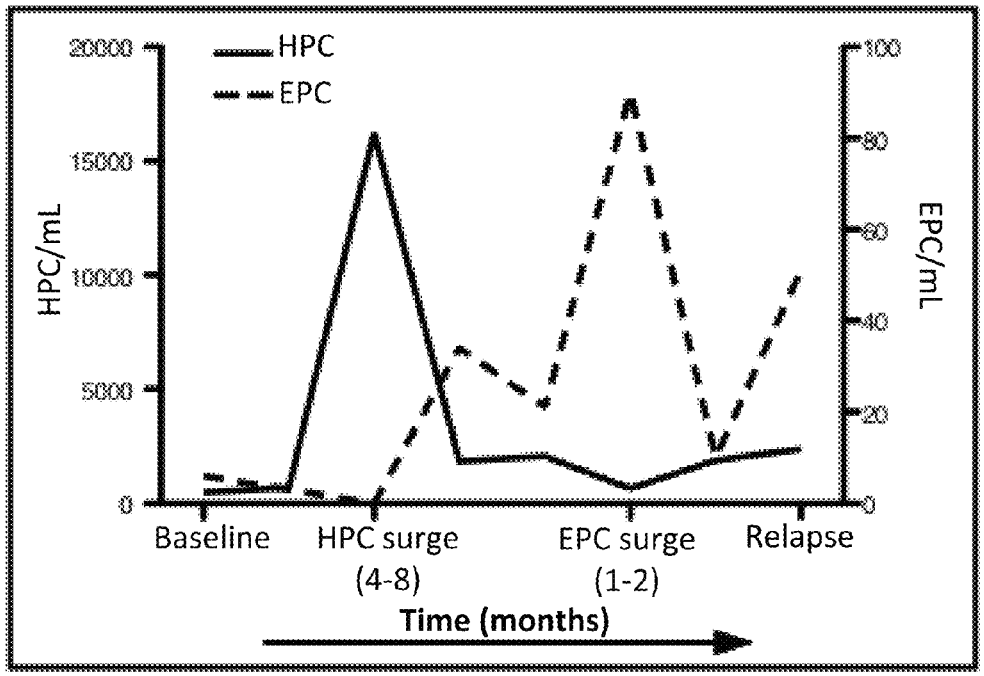
FIG. 3: Characteristic pattern of VEGFR1$^+$ and VEGFR2$^+$ hemangiogenic progenitor cells is observed prior to relapse of breast cancer who are without evidence of disease at study entry. An initial surge of VEGFR1$^+$HPCs is followed by a surge of the VEGFR2$^+$ EPCs prior to overt relapse. Median values of baseline, HPC surge, EPC surge, and at relapse of relapsed patients (n=3) are shown here. Parenthesis, range in months prior to overt relapse.

Incremental Rise in VEGFR1+ HPCs and VEGFR2+ EPCs Predicts Relapse in Patients with Breast Cancer Who have No Evidence of Disease In the 7 patients that developed relapse without prior evidence of disease, the median HPC/mL increased from baseline of 645.8 (range 23.5 to 1,914) to 2,899 (range 1,176 to 37,336) prior to relapse, p=0.016 (FIG. 2A). Similarly, median EPC/mL increased from baseline of 21.3 (range 4.7 to 42.5) to 94.7 (range 28.2 to 201.3) immediately prior to relapse p=0.016 (FIG. 2B). From the 4 patients from Study 2, monthly specimens were obtained enabling a look at the temporal relation of HPCs and EPCs prior to relapse (Table II). In these patients, an identical pattern in the progenitor cells emerged which heralded a relapse of breast cancer. An initial surge followed by a decline in HPCs and subsequent increase in EPCs preceded an overt recurrence (FIG. 3). In these patients, the median time between a surge in HPCs and EPCs prior to overt relapse was 6 months (range 4 to 8) and 1 month (range 1 to 2), respectively. Because the HPC surge antedating relapse is between 4 and 8 months, the 3 patients who relapsed within 2 months of study entry were actively relapsing at that time hence were excluded from this analysis.

TABLE II

HPC and EPC levels by patient

|  | pre HPC surge | HPC surge | post HPC surge | pre EPC surge | EPC surge | post EPC surge |
|---|---|---|---|---|---|---|
| patient 1 | 0.409 | 1.579 | 0.875 | 0.042498938 | 0.157751037 |  |
| patient 2 | 0.403 | 2.899 | 1.857 | 0.021310777 | 0.090206782 | 0.01 |
| patient 3 | 16.29 | 34.94 | 2.81 | 0.11 | 0.20 | 0.03 |
| patient 4 | 0.70 | 16.23 | 1.26 | 0.009 | 0.050 | 0.000 |
| median | 0.554 | 9.565 | 1.561 | 0.031904857 | 0.123978909 | 0.01 |

Figure 4:
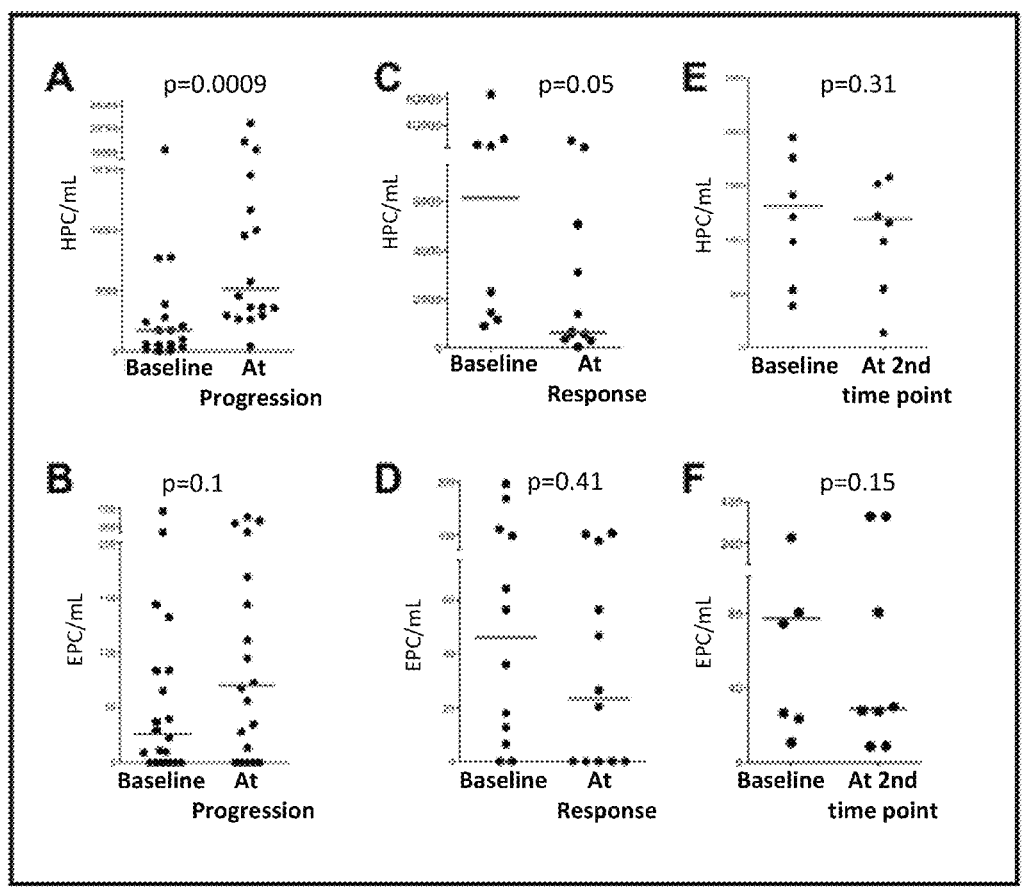
FIGS. 4A-4F: Change in VEGFR2$^+$ HPCs and VEGFR2$^+$ EPCs from baseline to a subsequent time point stratified by response to therapy, as defined by (A,B) progression of disease, (C,D) responding disease, and (E,F) stable disease. 1 data point is outside the axis limits in (A,B) graphs and 2 in (C,D) graphs. Horizontal line, median values.

Incremental Rise in VEGFR1+ HPCs and VEGFR2+ EPCs Predicts Clinical Progression of Disease/Resistance to Treatment in Patients Undergoing Systemic Therapy Thirty patients with stage 4 breast cancer were enrolled into Cohort 2 of Study 1 and underwent evaluation at the initiation of therapy and at 3, 4 or 6-week intervals over the course of three years and 40 treatment cycles. Eight patients were not included in the final analysis due to death prior to subsequent sample collection (4 patients) and loss to follow up (4 patients). Since a normal range has not been previously established for bone marrow-derived progenitor cells, subsequent time points are required for comparison to baseline. Of the 22 evaluable patients, systemic treatment included chemotherapy alone (19 cycles), hormonal therapy (6 patients) and combinations of both with biologics (trastuzumab and/or lapatinib [11 patients], bevacizumab [2 patients], and dasatinib [2 patients]). HPCs and EPCs were analyzed in patients stratified by response as per RECIST (Table III). Patients with progressive disease representing 20 treatment cycles had a significant increase in HPCs preceding overt progression compared to the baseline values at the start of a new treatment (FIGS. 4A-4B). Median HPC/mL increased from baseline of 1,696 (range 10 to 16,470) to 5,124 (range 374 to 77,605) prior to progression, p=0.0009. Median EPC/mL increased from baseline of 26 (range 0 to 560) to 71 (range 0 to 615) prior to progression, p=0.10. The median time between baseline and the increase in HPCs and EPCs was 7.5 weeks (range 4 to 88). There were no significant changes in these patients' median absolute lymphocyte count (ALC)/mL after receiving chemotherapy, 1,255 (range 500 to 2,800) at baseline and 1,450 (range 470 to 3,460) after chemotherapy, p=0.08.

TABLE III

Median VEGFR1+HPC/mL and VEGFR2+ EPC/mL by therapeutic response in stage 4 patients.

| Clinical Response t = 40 | Median HPC/mL Baseline | Response | p-value | Median EPC/mL Baseline | Response | p-value |
|---|---|---|---|---|---|---|
| Responding disease t = 12 | 6147 | 633 | 0.05 | 46 | 23 | 0.41 |
| Range | 912-85070 | 47-18065 | | 0-197 | 0-105 | |
| Stable disease t = 8 | 1309 | 1188 | 0.31 | 78 | 29 | 0.15 |
| Range | 390-55377 | 135-20690 | | 11-484 | 9-331 | |
| Progression of disease t = 20 | 1696 | 5124 | 0.0009 | 26 | 71 | 0.10 |
| Range | 10-16470 | 374-77605 | | 0-560 | 0-615 | |

Decrease in VEGFR1+ HPCs and VEGFR2+ EPCs Predicts Clinical Response to Systemic Therapy Eleven patients with breast cancer metastases representing 12 treatment cycles that were responding to systemic therapy had a reduction in median HPC and EPC values (FIGS. 4C-4D). Median HPC/mL decreased from baseline of 6,147 (range 912 to 85,070) to 633 (range 47 to 18,065) at response, p=0.05. A trend was seen for decreased median EPC/mL; 46 (range 0 to 197) at baseline decreased to 23 (range 0 to 105) at response, p=0.41. The median time between baseline and the decrease in HPCs and EPCs was 6 weeks (range 4 to 23). Median ALC/mL did not significantly change after chemotherapy in this group, 1,150 (range 600 to 3,400) at baseline and 1,250 (range 260 to 2,800) after chemotherapy, p=0.53.

Five patients with clinically stable disease after 8 treatment cycles did not have a significant change in either progenitor cells from baseline to a post-treatment time point, (median 9 weeks, range 8.5 to 32.5, FIGS. 4E-4F). HPC/mL remained stable at 1,309 (range 390 to 55,377) at baseline compared to 1,188 (range 135 to 20,690) at a post-treatment time point, p=0.31. EPC/mL decreased from 78 (range 11 to 484) at baseline to 29 (range 9 to 331) at a posttreatment time point, though this did not reach statistical significance, p=0.15. Similarly median ALC/mL did not significantly change: 1,235 (range 1,000 to 2,300) to 1,450 (720 to 2,300), p=0.7.

Discussion

Understanding the metastatic process is critical in eradicating cancer deaths. In this study, the inventors identified terminal events leading to the development of overt metastases in well-defined cohorts of breast cancer patients. The inventors have found a substantial increase in the VEGFR1+ HPCs months before relapse followed by a surge in the VEGFR2+ EPCs immediately preceding an overt relapse of cancer. Without being bound, the surge of HPCs in advance of the arrival of circulating EPCs is thought to represent initiation of the pre-metastatic niche, with an overt relapse occurring after EPCs "turn on" the angiogenic switch. This characteristic pattern was observed in patients without objective evidence of disease that relapsed as well as patients with established metastasis who progressed on therapy. In the 92 patients without evidence of disease who remained relapse-free throughout the study, this pattern in HPCs and EPCs was not observed. These observations confirm the preclinical models of metastases in breast cancer patients.

Furthermore, levels of circulating HPCs in patients with overt clinical metastases predicted therapeutic response. The change in HPCs was most significant in treatment-refractory tumors (progression of disease group) suggesting that active tumor neoangiogenesis is being driven by these cells. In fact, immediately prior to a patient's death, the levels of HPCs in addition to EPCs were several-fold higher than at any time earlier in the patient's treatment course. In treatment-sensitive tumors (responding disease group), a significant reduction in HPCs was observed with therapy. The absolute lymphocyte count in these patients remained stable during treatment, therefore it is unlikely that the marrow suppressive effects of the chemotherapy contributed to the decrease in HPCs observed. A significant change in EPCs did not occur in either group, although there was a trend for increased EPCs in the progression of disease group and decreased EPCs in the responding group. This could be due to timing of the specimen as the angiogenic switch is a dynamic process, and a subsequent examination of EPCs even a week later may have revealed a further change that reached statistical significance. It is unclear if chemotherapy-induced EPC mobilization, described in mouse models and human patients may have contributed (Shaked Y, et al., Cancer Cell; 14: 263-73 (2008), Farace F, et al., Ann Oncol; 18: 1421-2 (2007)). The change in HPCs might be the more robust marker to monitor for therapeutic response. Finally, as expected with the current model, in patients with disease that remained stable on therapy, there were no significant changes in either HPCs or EPCs.

It is important to acknowledge the difficulties in analyzing these progenitor cells. The lack of a consensus in defining the HPC and EPC phenotype or the optimal method to assay these cells may impact accurate quantification. The rarity of these cells in the peripheral circulation, constituting less than 0.0001-0.01% of peripheral circulating mononuclear cells, further underscores this difficulty (Khan S S, et al., Cytometry B Clin Cytom; 64: 1-8 (2005)). EPC levels may be affected by several factors including medications, growth factors, and common comorbidities such as cardiovascular disease (Bahlmann F H, et al., Blood; 103: 921-6 (2004), Friedrich E B, et al., Basic Res Cardiol; 104: 613-20 (2009)).

The data set presented herein is heavily annotated and controlled for these variables. Moreover, this study suggests that the relationship between these two distinct populations of BMD progenitor cells might be more important than the absolute values.

There is a clear advantage for the use of HPCs and EPCs as a clinical biomarker over the use of existing serum-based biomarkers (e.g., CEA and CA15-3), as the latter does not predict relapse early in the metastatic process and is a relatively late-stage event. In this study, 9 of 14 patients in both the progression of disease and relapsed cohorts had an elevation of a tumor marker at least 2 months after the surge in HPCs. Conceivably, this change in BMD progenitor cells represents a sufficiently early step in metastatic progression that allows for the opportunity to intervene with targeted therapy to promote maintenance of tumor dormancy and prevention of relapse or progression. Several novel agents targeting BMD cells have been introduced into the clinical arena with promising data including cediranib, (pan-VEGFR inhibitor), ramucirumab (IMC-1121B, anti-VEGFR2 antibody) and IMC-18F1 (anti-VEGFR1 antibody) (Goss G D, et al., J Clin Oncol; 28: 49-55, Spratlin J L, et al., J Clin Oncol; 28: 780-7, Schwartz J D, et al., Cancer; 116:1027-32). Finally, Study 2 described here is an ongoing phase II clinical trial of an anti-angiogenic copper depletion compound, which is attempting to modulate the angiogenic switch through copper-dependent mechanisms, in high risk for relapse breast cancer patients. In this study, patients who became adequately copper-depleted had a significant reduction in EPCs from baseline (Jain S, et al., Proc Breast Cancer Symp.; abstr 297 (2010)). A clinical trial investigating ramucirumab, an anti-VEGFR2 antibody, and IMC-18F1, an anti-VEGFR1 antibody, in combination with capecitabine in women with metastatic breast cancer is underway and is expected to shed much insight into the role of these BMD progenitor cells and the effect of targeted therapy on outcome (ClinicalTrials.gov identifier: NCT01234402).

This is the first study to offer insight into the angiogenic switch in vivo, specifically in de novo relapse and progression of breast cancer metastases. Circulating HPCs and EPCs are now shown to serve as a biomarker to predict relapse or disease progression, as well as to serve as a therapeutic target for those at high risk of relapse.

Example 2—Copper Depletion

Study Design

This phase II, open-label, single-arm study was conducted to assess patients with breast cancer at high risk for relapse. Patients were enrolled on an Institutional Review Board approved trial (NCT00195091, 0903-882, 0309006307) at Weill Cornell Medical College (WCMC) Iris Cantor Breast Cancer Center. Written informed consent was obtained prior to undergoing any study-specific procedures in accordance with the Declaration of Helsinki.

Study Objectives

The primary objectives were to assess safety and changes in the number of EPCs in patients treated with Tetrathiomolybdate (TM). Secondary objectives were to evaluate progression-free survival (PFS), number of HPCs, and levels of plasma angiogenic factors and cytokines.

Patients

Female patients were eligible for inclusion in the study if they met the following criteria: at least 18 years of age; histologically confirmed breast cancer with a) stage 3, b) stage 4 with no evidence of disease (NED), or c) stage 2 triple-negative breast cancer; lack of radiographic, biochemical or physical evidence of recurrent breast cancer; at least 6 weeks from previous chemotherapy, biologic therapy, surgery, or radiation; ECOG performance status of 0 or 1; and adequate organ function (hemoglobin>10, ANC>1500, platelets>100,000, Cr<1.5× normal limits, total bilirubin<1.5× normal limits and AST/ALT<1.5× normal limits).

Stage 2 triple-negative breast cancer patients were included because their estimated risk of relapse is equivalent to stage 3 hormone-receptor-positive breast cancer patients. Concurrent hormonal therapy was permitted but patients could not receive concomitant biologic or chemotherapy. Screening studies performed within 4 weeks of study entry included a physical exam, laboratory studies (complete blood count, blood chemistries, hepatic profile, tumor markers (CEA, CA15-3) and imaging studies (computerized tomography [CT] of chest, abdomen and pelvis and bone scan or positron emission tomography [PET]/CT scan per physicians' choice).

Treatment

All treatment was administered on an outpatient basis. Clinical grade TM was purchased in bulk from the Aldrich Chemical Company (Milwaukee, Wis.) under IND #71380 held by Dr. Linda Vahdat. It was stored in 100 gram lots under argon as it is only stable for 8 weeks when exposed to air (Brewer G, et al., Arch Neurol.; 48:42-7 (1991)). Research pharmacists dispensed the appropriate dose of TM in gelatin capsules to patients every 4-8 weeks and maintained a careful inventory using the NCI Drug Accountability Record Form. Stability testing was performed on each new shipment and not less than 4 times per year.

TM was administered in two phases, induction and maintenance: A) Induction: Patients self-administered TM 180 mg by mouth daily in 4 divided doses until serum Cp levels decreased to a target range of 5-16 mg/dL. One month of TM therapy comprised 1 cycle. Cp levels were tested every 2 weeks for the first 4 weeks and then weekly until target Cp was reached. When Cp levels were within target range, patients were switched to the maintenance phase. B) Maintenance: TM 100 mg taken daily in divided doses. Patients were followed every 2 weeks for 4 weeks to ensure Cp levels were stable then every 4 weeks. Dose reductions in 20 mg increments were allowed to minimize toxicity. Dose increases in 20 mg increments were allowed every 2 weeks to keep Cp levels in target range. Patients were removed from study if they developed progression of disease, excessive toxicity or failed to become copper-depleted after dose intensification. Patients brought completed medication logs to each visit. The duration of the trial was 2 years.

Clinical and Radiographic Assessments

Patients were seen at baseline and every month thereafter for physical examination and laboratory studies including complete blood count, complete metabolic panel, tumor markers, and experimental studies. Patients underwent imaging of investigator's choice, CT of chest, abdomen, and pelvis or PET/CT every 6 months and as needed to assess for relapse, using Response Evaluation Criteria in Solid Tumors (RECIST).

Safety and Tolerability

The National Cancer Institute—Common Toxicity Criteria for Adverse Events (CTCAE) version 3.0 were used for toxicity and adverse event reporting. In the event of grade 3/4 toxicity, dosing was held until recovery. Treatment was resumed at the investigator's discretion at 50% of the previous dose. If recovery did not occur within 2 weeks, the patient was removed from study. In the event of grade 2 toxicity, the dose of TM was held until recovery and a new cycle could be initiated at 100%. If grade 2 toxicity recurred, dosing was held until recovery and the next cycle was resumed at 50%. All patients were available to be evaluated for toxicity.

Enumeration of Hemangiogenic Progenitor Cells

Figure 5:
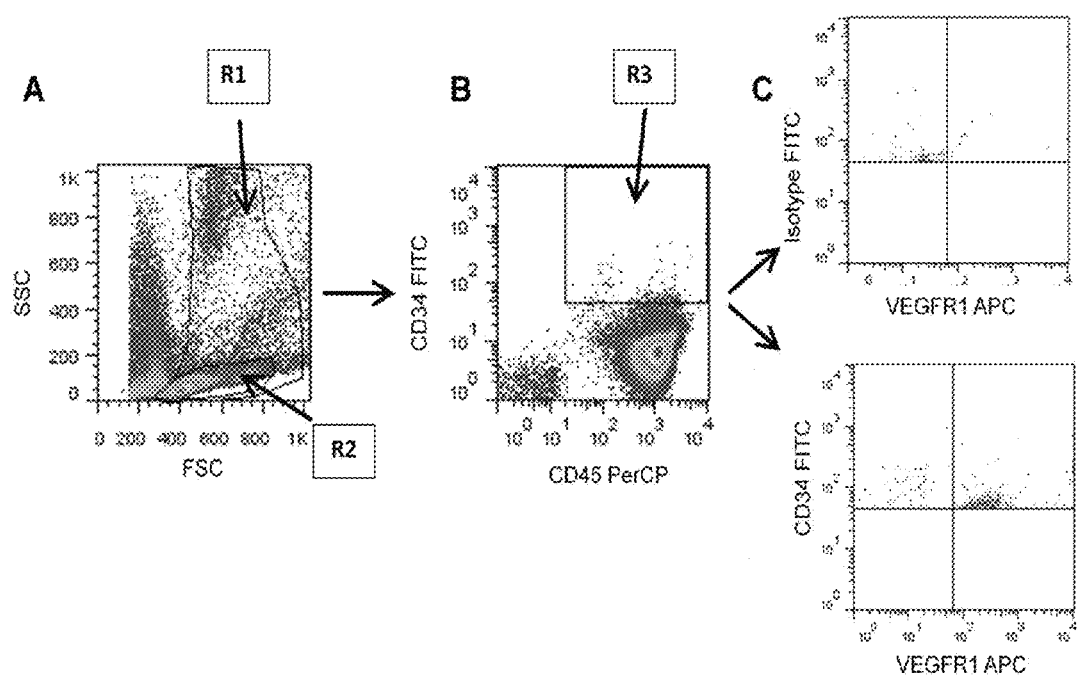
FIGS. 5A-5C: Hematopoietic progenitor cell (CD34$^+$/CD4.5$^+$/VEGFR1$^+$) enumeration: (A) The R1 gate was used to select the nucleated cell events, and the R2 gate was used to select lymphocyte events. (B) The R2 gate was used to select CD34$^+$, CD45$^+$ events from the R1 gate. (C) Quadrant gates were used to identify VEGFR1$^+$ events from the R3 gate: isotype control (upper panel) was used to accurately place the quadrant gate for CD34, VEGFR1 stained cells (lower panel). The absolute number of HPC's per mL of blood was calculated by multiplying the number of HPC events collected by a ratio of the absolute lymphocyte count/mL of the blood sample to the number of lymphocytes (determined by the R2 gating) in the collected data (HPC/mL=absolute lumphocyte count/mL×HPC events/number of events in lymphocyte gate).
Figure 6:
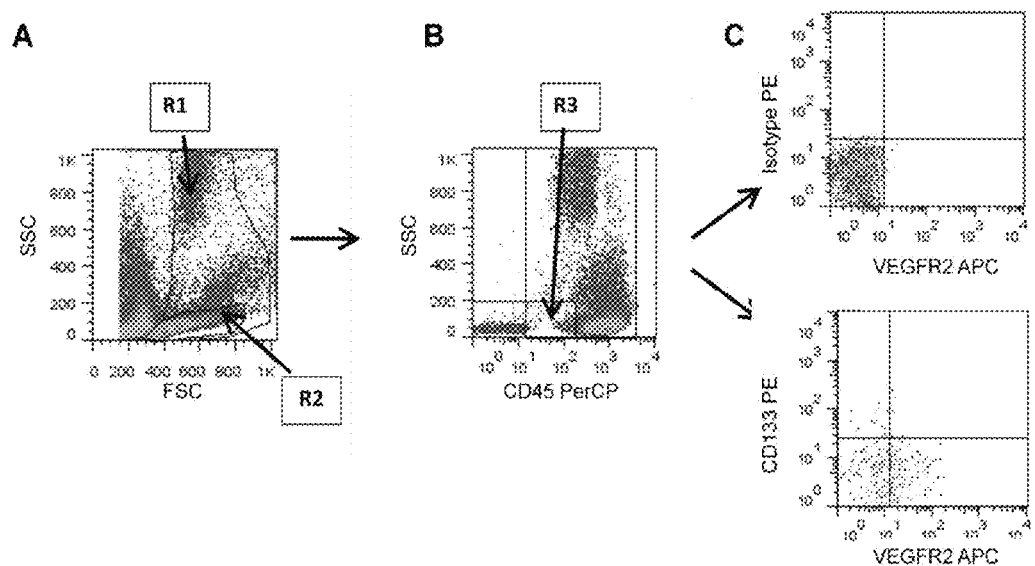
FIGS. 6A-6C: Endothelial progenitor cell (CD45$^{dim}$/CD133$^+$/VEGFR2$^+$) enumeration. (A) The R1 gate was used to select nucleated cell events, and the R2 gate was used to select lymphocyte events. (B) The R3 gate was used to select CD45$^{dim}$ events from the R1 gate. (C) Quadrant gates were used to identify CD133$^+$, VEGFR2$^+$ events from the R3 gate: isotype control (upper panel) was used to accurately place the quadrant gate for the VEGFR2, CD133 stained cells (lower panel). The absolute number of EPC's per mL of blood was calculated by multiplying the number of EPC events collected by a ratio of the absolute lymphocyte count/mL of the blood sample to the number of lymphocytes (determined by the R2 gating) in the collected data (EPC/mL=absolute lymphocyte count/mL×EPC events/number of events in lymphocyte gate).

Ten to 20 mL of venous blood were collected in EDTA-containing tubes and processed within 12 hours. Peripheral blood mononuclear cells were isolated by Ficoll density-gradient centrifugation. To quantitate circulating EPCs, cells were stained with CD133-PE (Miltenyi Biotec, Auburn, Calif.), VEGFR2-APC (R&D Systems, Minneapolis, Minn.), and CD45-PerCP (BD Biosciences, Franklin Lakes, N.J.). To quantitate HPCs, cells were stained with CD34-FITC (BD Biosciences), VEGFR1-APC (R&D Systems), and CD45-PerCP (BD Biosciences). An aliquot of cells was also stained with the appropriate isotype controls (mouse anti-human IgG1k). Samples were analyzed using a FACSCalibur flow cytometer (Bectin Dickinson, San Jose, Calif.). Three hundred thousand events were collected in the nucleated cell gate (excludes debris and platelets). Data analysis was done using FlowJo software (FlowJo, Ashland, Oreg.). A series of consecutive gates were made to include and exclude acquired events to quantitate specific populations such as $CD45^+$, $CD34^+$, $VEGFR1^+$. The number of EPCs and HPCs per mL of blood was calculated as follows: HPC/mL=(# HPC events/# lymphocyte events)×absolute lymphocyte count (lymphocytes/mL). EPC/mL=(# EPC events/# lymphocyte events)×absolute lymphocyte count (lymphocytes/mL). HPCs were defined as $CD45^+$, $CD34^+$, $VEGFR1^+$ (FIGS. 5A-5C). EPCs were defined as $CD45^{dim}$, $CD133^+$, $VEGFR2^+$ (FIGS. 6A-6C).

Angiogenic Factors and Cytokine Profiling

Plasma SDF-1 was detected by enzyme-linked immunosorbent assay (R&D Systems) according to manufacturer's protocol. Plasma levels of c-kit, VEGF, VEGFR1, VEGFR2, bFGF, and PIGF were detected by multiplex assay (Meso Scale Discovery, Gaithersburg, Md.) per manufacturer protocol.

Statistical Analysis

The intent-to-treat (ITT) population consisted of all patients who received at least one dose of TM. One patient did not take TM after enrollment due to personal preference. The following outcomes were recorded: toxicity attributable to TM, time to progression of disease, number of circulating hemangiogenic progenitor cells, serum markers of angiogenesis. Descriptive statistics for demographic and angiogenic variables were calculated for all patients. Incidence of adverse events and their associated 95% confidence intervals were estimated using standard methods for proportions. PFS was analyzed using survival analysis techniques. Median $VEGFR1^+$ and $VEGFR2^+$ values were computed at baseline and compared to subsequent time points by the Wilcoxon signed-rank. All p-values were two-sided with statistical significance evaluated at the 0.05 alpha level. All analyses were performed in SPSS Version 18.0 (SPSS Inc., Chicago, Ill.). The mixed model approach to repeated measures analysis of variance (RMANOVA) was carried out to determine significant changes over time in serum markers of angiogenesis. Multivariate analysis was done to control for standard clinical and pathologic factors.

Results:

Patient Characteristics

Between Jun. 1, 2007 and Jun. 30, 2010, 40 patients were enrolled. Twenty-seven patients remain currently on study. Reasons for discontinuation from the study include progression of disease (6), toxicity (3) and patient preference (2) and lost to followup (1). The median age was 50 years (range 29 to 66) and more than half of patients (65%) had an ECOG performance status of 0 at baseline. The majority of patients had a very high risk of relapse (i.e. exceeding 60% relapse risk at 10 years) including any subtype of stage 4 NED (30%), stage 3 triple-negative (12.5%), and stage 3 HER2-enriched (17.5%) breast cancer. Of the 28 adjuvant patients, 26 (92.9%) had received anthracycline and/or taxane, 7 (17.5%) had received trastuzumab, and 2 (5%) had received high-dose chemotherapy followed by stem cell support. Twenty-six (65%) patients were receiving concomitant endocrine therapy while on the trial. The metastatic cohort had received a median of 0 chemotherapy regimens (range 0-1).

Ceruloplasmin (Cp) Levels

Figure 7:
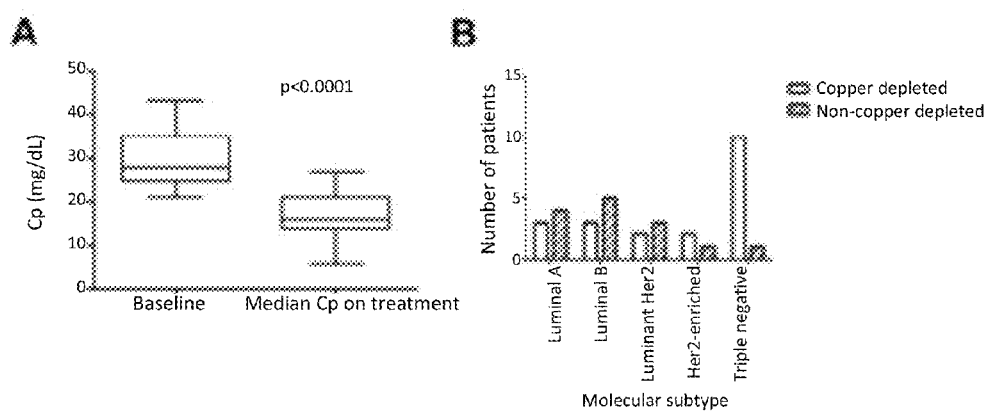
FIGS. 7A-7B: (A) ceruloplasmin (Cp) of patients in study. (B) Copper reduction in TNBC patients compared to other subtypes.
Figure 8:
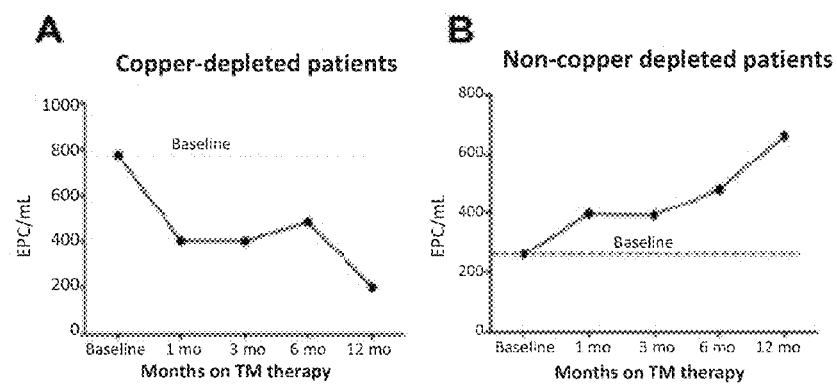
FIGS. 8A-8B: (A) EPC decrease with copper depletion (B) no decrease in EPC in copper-normal state.
Figure 9:
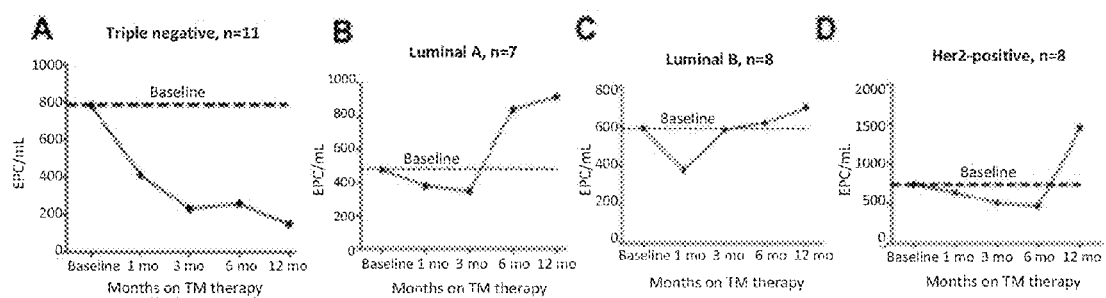
FIGS. 9A-9D: In copper depleted cohort a large and sustained decrease in EPCs is observed in the triple negative BC cohort (A); compared to the luminal A (B); luminal B (C); and HER 2neu subtypes (D).

The ITT population consisted of 39 patients. Median baseline Cp level was 29.7 mg/dL (range 21 to 47), which decreased to a mean Cp level of 14.2 mg/dL (range 7 to 26) at a median of 4 weeks. Target for copper depletion was defined as Cp below 17 mg/dL. Of those who took at least one dose of TM, 59% (23/40) of patients were effectively copper depleted and 15 patients (37.5%) were unable to be copper depleted. Mean Cp of copper depleted pts and non-copper depleted patients was 13.5 and 22.3 mg/dL, respectively (FIG. 1a). Patients spent a median of 78% of time (range 58 to 100%) within target Cp levels during the study . . . . Patients with triple-negative disease had a lower Cp at baseline (mean 25.9 mg/dL) compared to patients with hormone-receptor-positive cancer (31.7). 91% of triple-negative patients successfully copper depleted compared to the hormone-receptor subtypes (38-43%) and HER2-positive subtypes (40-67%) (FIG. 7B). Those on tamoxifen (n=10) had a higher baseline Cp level of 35.9 mg/dL (range 29-47) compared to 27.8 (22-36) on aromatase inhibitors (n=13). Mixed effects linear models of Cp over time showed a significant association with type of concomitant hormone therapy (p=0.006) and coadministration of a proton pump inhibitor (PPI; p=0.011), and significant interaction EPC Levels The median baseline number of 0.0398 cells/uL (range 0-0.21), which decreased over time to 0.0363 (range 0-0.18) at 1 year of TM therapy (FIG. 8A). The majority of patients' EPCs were maintained below baseline when Cp was in the target range. High-risk subtypes (triple negative, HER2-positive, and stage 4 NED) had higher EPC/uL levels at baseline (0.0456, range 0-0.207) compared to the hormone-receptor-positive stage 3 patients (0.0277, range 0-0.114) with more rapid decreases in EPC counts in response to copper depletion (FIG. 3). In 4 of 6 patients who developed a relapse while on study, a significant EPC rise preceded a tumor marker rise and objective relapse by 6 months.

Mixed effects linear models of EPCs over time showed a significant association with type of concomitant hormone therapy (p=0.0073) and coadministration of a proton pump inhibitor (PPI; p=0.0030) similar to Cp levels. There was also a significant interaction between type of hormone therapy, PPI use, or time (p<0.0001).

Toxicity

Overall TM was well tolerated with few adverse events. 426 cycles of TM were administered to 39 patients in the first 12 months of therapy. Of the 39 patients in the ITT population, 3 (7.7%) experienced dose interruptions, delays, reductions, or omissions due to toxicity during the study. There were no treatment-related deaths.

67 (15.7%) cycles were complicated by grade ½ neutropenia in 23 (59.0%) patients and 13 (3.1%) cycles by grade ¾ neutropenia in 9 (23.1%) patients. TM was held for 5 to 13 days until resolution of neutropenia and then resumed at a lower dose. One patient required hospital admission for neutropenic fever and was subsequently removed from the study. 50 (11.7%) cycles were complicated by grade ½ anemia in 14 (35.9%) patients. Only 1 (0.2%) cycle was affected by grade 3 anemia in a patient later diagnosed with B12 deficiency. There were no grade 4 incidences of anemia. No patients required growth factor support.

Non-Hematologic Toxicity:

There was no grade 3 or 4 non-hematologic toxicity. Eight patients had grade 1 or 2 gastrointestinal toxicity (nausea, vomiting or diarrhea) managed with dose adjustment alone. One patient with grade 2 diarrhea due to lactose used as a filler in the TM pills left the study. Sulfurous eructations affected 79 (18.5%) of cycles, which resolved with initiation of a PPI in >90% of patients. Grade 1 fatigue and peripheral neuropathy were seen in 29 (6.8%) and 6 (1.4%) cycles, respectively.

Clinical Outcomes

Six patients (15%) developed recurrence while on first 12 months of study. Three of these patients had stage 3 disease (1 triple-negative) and relapsed after 2, 3, and 10 months of TM. Three patients with stage 4 NED (1 triple-negative, 1 HER2-positive) relapsed after 1, 10, and 10 months of therapy. Of these 6 relapsed patients, Cp decreased to target in 4 patients and EPCs were maintained below baseline in only 1 patient while on TM therapy. In all patients, the 10-month PFS was 85.0% (95% CI, 74.6-96.8%). The 10-month PFS was lower in stage 4 NED patients compared to stage 2 and 3 patients (75.0 vs. 89.3%), and in triple-negative patients compared to hormone-receptor-positive patients (81.8 vs 85.7%).

HPCs and Serum Markers of Angiogenesis

There were no significant changes in HPCs in patients on TM. HPCs did not associate with any clinical factors including stage, molecular subtype, type of endocrine therapy, ability to copper deplete, age, BMI, or PPI use. SDF1, VEGFR2, and C-kit did not significantly change in patients while on therapy nor did they associate with Cp levels, EPC levels, relapse status, tumor or patient characteristics. In patients who relapsed, mean SDF1 increased from 2093 to 3052 pg/ml, whereas SDF1 in non-relapsed patients decreased from 1870 to 1811 pg/ml.

What is claimed is:

1. A method comprising measuring the level of VEGFR1$^+$ hematopoietic progenitor cells (HPCs) in a subject every one to three months until a surge is detected in the HPC levels, and measuring the level of VEGFR2$^+$ endothelial progenitor cells (EPCs) in said subject every one to three months until about 8 months after the surge in HPC levels.

2. The method of claim 1, wherein the HPCs are VEGFR1$^+$CD45$^+$CD34$^+$.

3. The method of claim 1, wherein the surge of at least two-fold in the level of HPCs and the level of EPCs is detected.

4. The method of claim 1, wherein said EPCs are VEGFR2$^+$CD133$^+$CD45$^{dim}$ endothelial progenitor cells (EPCs).

5. The method of claim 1, further comprising
diagnosing said subject as having an increased risk of progression or relapse of breast cancer when a surge in the level of HPCs followed by a surge in the level of EPCs is detected; and
administering an effective amount of an HPC antagonist and an EPC antagonist to the subject after the diagnosis.

6. The method of claim 5, wherein a surge in the level of HPCs followed by a surge in the level of EPCs indicates an increased risk of cancer progression or relapse to occur within one year from the surge in the level of HPCs and within four months of said surge in the level of EPCs.

7. The method of claim 1, wherein the level of HPCs and the level of EPCs are measured every two months.

8. The method of claim 1, wherein the sample is selected from blood, saliva, or tissue from said subject.

9. The method of claim 1, wherein the level of HPCs and the level of EPCs are measured every month.

* * * * *